(12) United States Patent
Canessa et al.

(10) Patent No.: US 8,285,083 B2
(45) Date of Patent: ***Oct. 9, 2012

(54) SYSTEM FOR REMOTELY GENERATING AND DISTRIBUTING DICOM-COMPLIANT MEDIA VOLUMES

(75) Inventors: John C. Canessa, Apple Valley, MN (US); Giancarlo Canessa, Eagan, MN (US); Gino Canessa, Eagan, MN (US)

(73) Assignee: Datcard Systems, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/026,082

(22) Filed: Feb. 11, 2011

(65) Prior Publication Data

US 2011/0176748 A1    Jul. 21, 2011

Related U.S. Application Data

(63) Continuation of application No. 11/740,062, filed on Apr. 25, 2007, now Pat. No. 7,933,472.

(60) Provisional application No. 60/795,141, filed on Apr. 26, 2006.

(51) Int. Cl.
*G06K 9/54* (2006.01)

(52) U.S. Cl. ....................................... 382/305

(58) Field of Classification Search ................ 382/128, 382/132, 305; 705/2, 3, 4, 1.1
See application file for complete search history.

(56) References Cited

U.S. PATENT DOCUMENTS

| | | |
|---|---|---|
| 4,491,725 A | 1/1985 | Pritchard |
| 4,736,256 A | 4/1988 | Ichikawa |
| 4,768,099 A | 8/1988 | Mukai |
| 4,852,570 A | 8/1989 | Levine |
| 4,860,112 A | 8/1989 | Nichols et al. |
| 4,874,935 A | 10/1989 | Younger |
| 4,945,410 A | 7/1990 | Walling |
| 4,958,283 A | 9/1990 | Tawara et al. |
| 5,002,062 A | 3/1991 | Suzuki |
| 5,005,126 A | 4/1991 | Haskin |
| 5,019,975 A | 5/1991 | Mukai |
| 5,208,802 A | 5/1993 | Suzuki et al. |
| 5,235,510 A | 8/1993 | Yamada et al. |
| 5,272,625 A | 12/1993 | Nishihara et al. |
| 5,291,399 A | 3/1994 | Chaco |

(Continued)

FOREIGN PATENT DOCUMENTS

CA    2 322 191    4/2000

(Continued)

OTHER PUBLICATIONS

Kohn D et al., Mail and Messaging Software: M&Ms of Communication—A Treat for Health Care Information Systems, 1996 Annual HIMSS Conference and Exhibition.

(Continued)

*Primary Examiner* — Yon Couso
(74) *Attorney, Agent, or Firm* — Knobbe, Martens, Olson & Bear LLP

(57) ABSTRACT

A system for generating digital image media volumes includes a digital image terminal for receiving, processing, and transmitting digital image data, and being adapted for processing the digital image data into one or more discrete DICOM-standard data objects. The system further includes a media volume production facility remotely located from the digital image terminal, and communicatively coupled to the digital image terminal via a server-operated computer network.

12 Claims, 2 Drawing Sheets

U.S. PATENT DOCUMENTS

| | | |
|---|---|---|
| 5,317,337 A | 5/1994 | Ewaldt |
| 5,319,543 A | 6/1994 | Wilhelm |
| 5,321,520 A | 6/1994 | Inga et al. |
| 5,321,681 A | 6/1994 | Ramsay et al. |
| 5,384,643 A | 1/1995 | Inga et al. |
| 5,410,676 A | 4/1995 | Huang et al. |
| 5,416,602 A | 5/1995 | Inga et al. |
| 5,451,763 A | 9/1995 | Pickett et al. |
| 5,452,416 A | 9/1995 | Hilton et al. |
| 5,469,353 A | 11/1995 | Pinsky et al. |
| 5,499,293 A | 3/1996 | Behram et al. |
| 5,502,726 A | 3/1996 | Fischer |
| 5,513,101 A | 4/1996 | Pinsky et al. |
| 5,518,325 A | 5/1996 | Kahle |
| 5,531,227 A | 7/1996 | Schneider |
| 5,542,768 A | 8/1996 | Rother et al. |
| 5,544,649 A | 8/1996 | David et al. |
| 5,572,422 A | 11/1996 | Nematbakhsh et al. |
| 5,581,460 A | 12/1996 | Kotake et al. |
| 5,586,262 A | 12/1996 | Komatsu et al. |
| 5,592,511 A | 1/1997 | Schoen et al. |
| 5,597,182 A | 1/1997 | Reber et al. |
| 5,597,995 A | 1/1997 | Williams et al. |
| 5,605,153 A | 2/1997 | Fujioka et al. |
| 5,633,839 A | 5/1997 | Alexander et al. |
| 5,634,053 A | 5/1997 | Noble et al. |
| 5,655,084 A | 8/1997 | Pinsky et al. |
| 5,659,741 A | 8/1997 | Eberhardt |
| 5,668,998 A | 9/1997 | Mason et al. |
| 5,671,353 A | 9/1997 | Tian et al. |
| 5,687,717 A | 11/1997 | Halpern et al. |
| 5,717,841 A | 2/1998 | Farrell et al. |
| 5,721,891 A | 2/1998 | Murray |
| 5,724,582 A | 3/1998 | Pelanek et al. |
| 5,734,629 A | 3/1998 | Lee et al. |
| 5,734,915 A | 3/1998 | Roewer |
| 5,740,134 A | 4/1998 | Peterson |
| 5,763,862 A | 6/1998 | Jachimowicz et al. |
| 5,781,221 A | 7/1998 | Wen et al. |
| 5,796,862 A | 8/1998 | Pawlicki et al. |
| 5,809,243 A | 9/1998 | Rostoker et al. |
| 5,822,544 A | 10/1998 | Chaco et al. |
| 5,823,948 A | 10/1998 | Ross, Jr. et al. |
| 5,832,488 A | 11/1998 | Eberhardt |
| 5,848,198 A | 12/1998 | Penn |
| 5,859,628 A | 1/1999 | Ross et al. |
| 5,867,795 A | 2/1999 | Novis et al. |
| 5,867,821 A | 2/1999 | Ballantyne et al. |
| 5,869,163 A | 2/1999 | Smith et al. |
| 5,873,824 A | 2/1999 | Doi et al. |
| 5,882,555 A | 3/1999 | Rohde et al. |
| 5,884,271 A | 3/1999 | Pitroda |
| 5,899,998 A | 5/1999 | McGauley et al. |
| 5,903,889 A | 5/1999 | de la Huerga et al. |
| 5,909,551 A | 6/1999 | Tahara et al. |
| 5,911,687 A | 6/1999 | Sato et al. |
| 5,914,918 A | 6/1999 | Lee et al. |
| 5,920,317 A | 7/1999 | McDonald |
| 5,924,074 A | 7/1999 | Evans |
| 5,942,165 A | 8/1999 | Sabatini |
| 5,946,216 A | 8/1999 | Hollerich |
| 5,946,276 A | 8/1999 | Ridges et al. |
| 5,949,491 A | 9/1999 | Callahan et al. |
| 5,950,207 A | 9/1999 | Mortimore et al. |
| 5,951,819 A | 9/1999 | Hummell et al. |
| 5,974,004 A | 10/1999 | Dockes et al. |
| 5,974,201 A | 10/1999 | Chang et al. |
| 5,982,736 A | 11/1999 | Pierson |
| 5,995,077 A | 11/1999 | Wilcox et al. |
| 5,995,345 A | 11/1999 | Overbo |
| 5,995,965 A | 11/1999 | Experton |
| 6,006,191 A | 12/1999 | DiRienzo |
| 6,021,404 A | 2/2000 | Moukheibir |
| 6,022,315 A | 2/2000 | Iliff |
| 6,032,120 A | 2/2000 | Rock et al. |
| 6,041,703 A | 3/2000 | Salisbury et al. |
| 6,063,030 A | 5/2000 | Vara et al. |
| 6,067,075 A | 5/2000 | Pelanek |
| 6,115,486 A | 9/2000 | Cantoni |
| 6,131,090 A | 10/2000 | Basso, Jr. et al. |
| 6,137,527 A | 10/2000 | Abdel-Malek et al. |
| 6,148,331 A | 11/2000 | Parry |
| 6,149,440 A | 11/2000 | Clark et al. |
| 6,155,409 A | 12/2000 | Hettinger |
| 6,157,914 A | 12/2000 | Seto et al. |
| 6,188,782 B1 | 2/2001 | Le Beux |
| 6,241,668 B1 | 6/2001 | Herzog |
| 6,260,021 B1 | 7/2001 | Wong et al. |
| 6,272,235 B1 | 8/2001 | Bacus et al. |
| 6,272,470 B1 | 8/2001 | Teshima |
| 6,363,392 B1 | 3/2002 | Halstead et al. |
| 6,366,966 B1 | 4/2002 | Laney et al. |
| 6,397,224 B1 | 5/2002 | Zubeldia et al. |
| 6,415,295 B1 | 7/2002 | Feinberg |
| 6,454,705 B1 | 9/2002 | Cosentino et al. |
| 6,496,744 B1 | 12/2002 | Cook |
| 6,529,757 B1 | 3/2003 | Patel et al. |
| 6,564,256 B1 | 5/2003 | Tanaka |
| 6,564,336 B1 | 5/2003 | Majkowski |
| 6,574,629 B1 | 6/2003 | Cooke, Jr. et al. |
| 6,574,742 B1 | 6/2003 | Jamroga et al. |
| 6,591,242 B1 | 7/2003 | Karp et al. |
| 6,606,171 B1 | 8/2003 | Renk et al. |
| 6,615,192 B1 | 9/2003 | Tagawa et al. |
| 6,633,674 B1 | 10/2003 | Barnes et al. |
| 6,654,724 B1 | 11/2003 | Rubin et al. |
| 6,671,714 B1 | 12/2003 | Weyer et al. |
| 6,675,271 B1 | 1/2004 | Xu et al. |
| 6,678,703 B2 | 1/2004 | Rothschild et al. |
| 6,678,764 B2 | 1/2004 | Parvulescu et al. |
| 6,760,755 B1 | 7/2004 | Brackett |
| 6,847,933 B1 | 1/2005 | Hastings |
| 6,910,038 B1 | 6/2005 | James |
| 6,925,319 B2 | 8/2005 | McKinnon |
| 6,954,767 B1 | 10/2005 | Kanada |
| 6,954,802 B2 | 10/2005 | Sutherland et al. |
| 6,988,074 B2 | 1/2006 | Koritzinsky et al. |
| 7,006,881 B1 | 2/2006 | Hoffberg et al. |
| 7,020,651 B2 | 3/2006 | Ripley |
| 7,111,015 B2 | 9/2006 | Aoyama |
| 7,120,644 B1 | 10/2006 | Canessa et al. |
| 7,194,119 B2 | 3/2007 | Zahlmann et al. |
| 7,268,794 B2 | 9/2007 | Honda et al. |
| 7,298,836 B2 | 11/2007 | Wellons et al. |
| 7,302,164 B2 | 11/2007 | Wright et al. |
| 7,382,255 B2 | 6/2008 | Chung et al. |
| 7,395,215 B2 | 7/2008 | Grushka |
| 7,483,839 B2 | 1/2009 | Mayaud |
| 7,523,489 B2 | 4/2009 | Bossemeyer et al. |
| 7,552,340 B2 | 6/2009 | Ooi et al. |
| 7,621,445 B2 | 11/2009 | Esseiva et al. |
| 7,640,271 B2 | 12/2009 | Logan |
| 7,694,331 B2 | 4/2010 | Vesikivi et al. |
| 7,729,597 B2 | 6/2010 | Wright et al. |
| 7,734,157 B2 | 6/2010 | Wright et al. |
| 7,783,173 B2 | 8/2010 | Wright et al. |
| 7,783,174 B2 | 8/2010 | Wright et al. |
| 7,801,422 B2 | 9/2010 | Wright et al. |
| 7,836,493 B2 | 11/2010 | Xia et al. |
| 7,965,408 B2 | 6/2011 | Samari-Kermani |
| 8,045,214 B2 | 10/2011 | Samari |
| 8,059,304 B2 | 11/2011 | Samari |
| 2001/0041991 A1 | 11/2001 | Segal et al. |
| 2001/0056359 A1 | 12/2001 | Abreu |
| 2002/0007287 A1 | 1/2002 | Straube et al. |
| 2002/0019751 A1 | 2/2002 | Rothschild et al. |
| 2002/0046061 A1 | 4/2002 | Wright et al. |
| 2002/0077861 A1 | 6/2002 | Hogan |
| 2002/0085476 A1 | 7/2002 | Samari-Kermani |
| 2002/0103675 A1 | 8/2002 | Vanelli |
| 2002/0103811 A1 | 8/2002 | Fankhauser et al. |
| 2002/0133373 A1 | 9/2002 | Silva-Craig et al. |
| 2002/0138301 A1 | 9/2002 | Karras et al. |
| 2002/0138524 A1 | 9/2002 | Ingle et al. |
| 2003/0040940 A1 | 2/2003 | Nehammer |
| 2003/0051144 A1 | 3/2003 | Williams |
| 2003/0105393 A1 | 6/2003 | Sutherland et al. |

| | | | |
|---|---|---|---|
| 2003/0200226 A1 | 10/2003 | Wells et al. | |
| 2003/0208382 A1 | 11/2003 | Westfall | |
| 2003/0220822 A1 | 11/2003 | Fiala et al. | |
| 2004/0006492 A1 | 1/2004 | Watanabe | |
| 2004/0078236 A1 | 4/2004 | Stoodley et al. | |
| 2004/0083123 A1 | 4/2004 | Kim et al. | |
| 2004/0210458 A1 | 10/2004 | Evans et al. | |
| 2004/0215637 A1 | 10/2004 | Kitamura et al. | |
| 2005/0075909 A1 | 4/2005 | Flagstad | |
| 2005/0125252 A1 | 6/2005 | Schoenberg | |
| 2005/0125254 A1 | 6/2005 | Schoenberg | |
| 2005/0125258 A1 | 6/2005 | Yellin et al. | |
| 2005/0154614 A1 | 7/2005 | Swanson et al. | |
| 2005/0192837 A1 | 9/2005 | Fears et al. | |
| 2005/0197860 A1 | 9/2005 | Joffe et al. | |
| 2005/0240445 A1 | 10/2005 | Sutherland et al. | |
| 2005/0267351 A1 | 12/2005 | Humphrey et al. | |
| 2006/0058626 A1 | 3/2006 | Weiss et al. | |
| 2006/0085226 A1 | 4/2006 | Kamber | |
| 2006/0149601 A1 | 7/2006 | Langhofer et al. | |
| 2006/0155584 A1 | 7/2006 | Aggarwal | |
| 2006/0161928 A1 | 7/2006 | Douglass et al. | |
| 2006/0179112 A1 | 8/2006 | Weyer et al. | |
| 2007/0050216 A1 | 3/2007 | Wright et al. | |
| 2007/0061170 A1 | 3/2007 | Lorsch | |
| 2007/0180509 A1 | 8/2007 | Swartz et al. | |
| 2008/0063368 A1 | 3/2008 | Wright et al. | |
| 2008/0071577 A1 | 3/2008 | Highley | |
| 2008/0122878 A1 | 5/2008 | Keefe et al. | |
| 2008/0172254 A1 | 7/2008 | Rosenfeld et al. | |
| 2008/0221920 A1 | 9/2008 | Courtney | |
| 2008/0319798 A1 | 12/2008 | Kelley | |
| 2009/0018871 A1 | 1/2009 | Essig et al. | |
| 2009/0055924 A1 | 2/2009 | Trotter | |
| 2009/0119764 A1 | 5/2009 | Applewhite et al. | |
| 2009/0198515 A1 | 8/2009 | Sawhney | |
| 2009/0204433 A1 | 8/2009 | Darian et al. | |
| 2010/0115288 A1 | 5/2010 | Monk et al. | |
| 2010/0138446 A1 | 6/2010 | Canessa et al. | |
| 2010/0286997 A1 | 11/2010 | Srinivasan | |

FOREIGN PATENT DOCUMENTS

| | | |
|---|---|---|
| DE | 198 02 572 A1 | 8/1999 |
| EP | 0 684 565 A1 | 11/1995 |
| EP | 0 781 032 A3 | 3/1999 |
| EP | 0 952 726 A1 | 10/1999 |
| GB | 2 096 440 A | 10/1982 |
| JP | 04-177473 A | 6/1992 |
| JP | 06-261892 A | 9/1994 |
| WO | WO 97/22297 | 6/1997 |
| WO | WO 00/02202 | 1/2000 |
| WO | WO 00/19416 | 4/2000 |

OTHER PUBLICATIONS

*Datcard v. Codonics* Civil Action No. SACV 08-00063 AHS, Declaration of J. Leavitt in Support of Codonics, Inc.'s Motion for Stay Pending Reexamination of the Patent-in-Suit and Ex Parte Application for an Order Shortening Time to File and Hear Codonics, Inc.'s Motion for Stay Pending Reexamination of the Patent-in-Suit, filed Dec. 12, 2008.
*Datcard v. Codonics* Civil Action No. SACV 08-00063 AHS, Declaration of J. Leavitt in Support of Codonics, Inc.'s Motion for Stay Pending Reexamination of the Patent-in-Suit, filed Dec. 29, 2008.
*Datcard v. Codonics* Civil Action No. SACV 08-00063 AHS, Declaration of L. Srnka in Support of Defendant Codonics, Inc.'s Reply in Support of Motion for Stay Pending Reexamination of the Patent-in-Suit, filed Jan. 26, 2009.
*Datcard v. Codonics* Civil Action No. SACV 08-00063 AHS, Declaration of M. Kendrick in Support of Motion to Compel Compliance with Subpoena, dated Jan. 15, 2009.
Kendrick MR, Declaration in Support of Request for Reexamination of U.S. Patent No. 7,302,164, Aug. 7, 2009.
*Datcard v. Codonics* Civil Action No. SACV 08-00063 AHS, Declaration of P. Nikolai in Support of Rimage's Opposition and Cross-Motion to Quash, dated Jan. 20, 2009.
*Datcard v. Codonics* Civil Action No. SACV 08-00063 AHS, Declaration of R. Wise in Support of Codonics' Reply to DatCard's Opposition to Codonics' Motion for Stay Pending Reexamination of the Patent-in-Suit, filed Jan. 26, 2009.
*Datcard v. Codonics* Civil Action No. SACV 08-00063 AHS, Defendant and Counterclaimant Codonics, Inc.'s First Amended Initial Disclosures, dated Jan. 29, 2009.
*Datcard v. Codonics* Civil Action No. SACV 08-00063 AHS, Defendant and Counterclaimant Codonics, Inc.'s Initial Disclosures, dated Apr. 16, 2008.
*Datcard v. Codonics* Civil Action No. SACV 08-00063 AHS, Defendant Codonics, Inc.'s Memorandum in Support of Motion to Compel Compliance with Subpoena to Rimage Corporation, dated Jan. 15, 2009.
Dejarnette Research Systems, DICOM/QR: DICOM Conformance Statement, 1997.
Dejarnette Research Systems, MediShare 1000 Worklist Manager: DICOM Conformance Statement, 1996.
Winstein D et al., Optimizing Clinical Information Systems in Complex Computing Environments, 1996 Annual HIMSS Conference and Exhibition.
Department of Veterans Affairs, DHCP integrated imaging project: Report of the evaluation panel, Jun. 8, 1990.
Shindoll D, Cover Story: Managing Risk in Planning and Implementing a PACS, Diagnostic Imaging, Jan. 1998, pp. 46-51.
Claesen S, DICOM 3.0 Public Doman Software, Dec. 21, 1995.
DICOM Birmingham 96, Tutorial Rev. 3.0, 1996.
SG&A Consulting, Inc. & Otech, Inc., DICOM Conformance Requirements for CT/MR Modalities, Version 1.0, Nov. 15, 1999.
ETIAM, DICOM Conformance Statement, WinSCP32 v2.42 Version 7, Nov. 2000.
Elion JL, DICOM Media Interchange Standards for Cardiology: Initial Interoperability Demonstration, Proceedings of the Nineteenth Annual Symposium on Computer Application in Medical Care, 1995, pp. 591-595.
Clunie D, DICOM Structured Reporting, 2000.
Heartlab Inc., DICOMwriter Product Webpage, 1999.
Soft-Copy Interpretation: How to Do It, What to Avoid, DI Forum, Sep. 1998, pp. 66-72.
Wong Awk et al., Digital archive system for radiologic images, RadioGraphics, Sep. 1994, pp. 1119-1126, vol. 14—No. 5.
Macura KJ et al., Digital case library: A resource for teaching, learning, and diagnosis support in radiology, RadioGraphics, Jan. 1995, pp. 155-164, vol. 15—No. 1.
ACR-NEMA Committee, Working Group V, Digital Imaging and Communications in Medicine (DICOM) Supplement 19 General Purpose CD-R Image Interchange Profile, Jan. 28, 1997.
DICOM Standards Committee, Working Group 5 Interchange Media, Digital Imaging and Communications in Medicine (DICOM) Supplement 40: DVD-RAM Media Application Profiles, May 18, 2001.
Sallfrank W, Digital networking and archiving with ACOM TOP, International Journal of Cardiac Imaging, 1998, pp. 323-327, vol. 14.
Ferdandez-Bayo J et al., Distributing medical images with internet technologies: A DICOM java viewer, RadioGraphics, Mar.-Apr. 2000, pp. 581-590, vol. 20—No. 2.
Huebner DP & Miller LR, Business Process Reengineering of an Outpatient Clinic Using Simulation, 1996 Annual HIMSS Conference and Exhibition.
Cahill DR et al., Sectional Anatomy Using the Personal Computer, Journal of Digital Imaging, Aug. 1997, p. 277, vol. 10—No. 3.
Tucker DM, Archives, Sep. 1999.
Department of the Army, Draft Specifications for Medical Diagnostic Imaging Support (MDIS) System, Apr. 4, 1990.
Spires E & Nacey G, Discharge Process Streamlined Through Interactive Voice Response Technology, 1996 Annual HIMSS Conference and Exhibition/.
Wong STC & Wong HK, Editorial, Computerized Medical Imaging and Graphics, Jul.-Aug. 1996, pp. 187-188, vol. 20—No. 4.
Barthell E et al., The National Information Infrastructure Health Information Network NII-HIN, 1996 Annual HIMSS Conference and Exhibition.

Sweeney EF et al., Successful Implementation of Procedural Outcome and Disease State Management Databases, 1996 Annual HIMSS Conference and Exhibition.

Walkley EI, Data-Based Assessment of Urgent Care in a Pediatric ED, 1996 Annual HIMSS Conference and Exhibition.

Smith EM, Project MICAS—Medical Information, Communication and Archive System: PACS Implementation at the University of Rochester Medical Center, Journal of Digital Imaging, Aug. 1997, p. 228, vol. 10—No. 3.

Remmlinger E & Newman MS, The Dating Game: Mergers, Affiliations, and Their Information Technology Implications, 1996 Annual HIMSS Conference and Exhibition.

Fisher M, Email from Michael Fisher at Mitra Imaging to Susanna Fries at Mitra Imaging, RE: Montreal Heart (ICM) Address for Vault, May 1, 1998.

*Datcard* v. *Codonics* Civil Action No. SACV 08-00063 AHS, Email generated by CM/ECF system re: Declaration (Motion related), Feb. 4, 2009.

*Datcard* v. *Codonics* Civil Action No. SACV 08-00063 AHS, Email generated by CM/ECF system re: Objection/Opposition (Motion related), Feb. 4, 2009.

Starrett RA, The New Dyes Cast: Mapping the CD-R Media Market—Includes Related Articles—Industry Overview, EMedia Professional, Oct. 1998.

Emerald Archiving Inc., Backfile Conversion Pricing for Huntsville Hospital, Mar. 21, 1999.

Hayes E, Case Study: PACS helps Mayo Practice Meet Urgent-Care Needs, Diagnostic Imaging, Sep. 1997, pp. P22-P24.

Mitra Imaging, Engineering Software Releases, Product Release Checklists, and Software Release Notes from Mitra Imaging to Electromed International, dated Sep. 5, 1997 to Sep. 12, 1997.

Khludov S, Dissertation, Entwicklung von Algorithmen und Programmen für ein Archivierungs- und Kommunikationssystem zur internetbasierten Verwaltung medizinischer Bilder, Aug. 1999, University of Trier.

Drazen E & Metzger J, Creating New Models for Ambulatory Practice: Efficient, Wellness-Focused, IT-Enabled, 1996 Annual HIMSS Conference and Exhibition.

ETIAM, DICOM 3.0 Conformance Statement: DICOM Eye v2.42 Version 1, dated Sep. 12, 2000.

Hanlon W et al., Evolution of the clinical review station for enterprise-wide multimedia radiology reporting, Proc. of SPIE, Feb. 2000, pp. 204-210, vol. 3980.

Sisk FA & Hampton BH, Report Cards: Are You Ready for Data Driven Competition, 1996 Annual HIMSS Conference and Exhibition.

Mosser H et al., Filmless digital radiology—feasibility and 20 month experience in clinical routine, Medical Informatics, 1994, pp. 149-159, vol. 19—No. 2.

ACC-ACR-NEMA, Final Text—Supplement 2, Digital Imaging and Communications in Medicine (DICOM), Part 11: Media Storage Application Profiles, Addenda on Conformance, Feb. 26, 1995.

Gross M & Lohman PM, Technology and Tactics of Physician Integration, HIMSS Proceedings, 1996, pp. 13-22, vol. 1.

Biddle MH et al., Integrating Telecommunications Systems Into the Evolving Health Care Delivery Environment, HIMSS Proceedings, 1996, pp. 112-119, vol. 1.

Zaidel M et al., Interactive Web-Based Radiology Teaching File, Journal of Digital Imaging, May 1999, pp. 203-204, vol. 12—No. 2.

Sutter MA and Baker JA, Redesigning the Medication Management System, HIMSS Proceedings, 1996, pp. 148-158, vol. 1.

Tecca MB & Garrett R, Radical Operating Improvement—A Rational Approach for Ongoing Results, HIMSS Proceedings, 1996, pp. 190-203, vol. 2.

Barrett MJ et al., Concept to Reality: Strategic Approach for Supporting Managed Care Needs, HIMSS Proceedings, 1996, pp. 72-86, vol. 1.

Anderson MP et al., US Food and Drug Administration's Regulation of Software and Picture Archiving and Communication Systems, Journal of Digital Imaging, Aug. 1997, p. 19, vol. 10—No. 3.

MEDASYS Digital Systems, DxWin 2.0 Evaluation Version, Readme.txt, 1997.

ALGOTEC, Med-e-Mail Technical Manual Version 1.0, 2001.

Tagare H et al., Medical image databases: a content-based retrieval approach, Journal of the American Medical Informatics Association, May/Jun. 1997, pp. 184-198, vol. 4—No. 3.

Product Showcase: Automated DICOM Exchange Station, Medical Imaging Magazine, Jan. 2000.

Medical Imaging Technology Associates, Preliminary Tapestry Users Guide, 1997.

Medical Imaging Technology Associates, Tapestry Read Me, May 9, 1997.

Medical Imaging Technology Associates, Tapestry Release Notes, May 8, 1997.

Medical Imaging Technology Associates, Tapestry Version 1.0 Medical Image Review Software Demonstration, Jan. 1997.

Medical Imaging web page for Image Archiving the ASP Way, Nov. 2000.

MEDIFACE, PiView™ 3.0 User's Guide, part 1, Sep. 1999.

MEDIFACE, PiView™ 3.0 User's Guide, part 2, Sep. 1999.

MEDIFACE, PiView™ 3.0 User's Guide, part 3, Sep. 1999.

MEDIFACE, PiView 3.0 (3.0.7.0) English Version, ReadMe.txt, Nov. 10, 1999.

MEDIFACE, PiView 3.0, DICOM Conformance Statement, Rev. 1.2-990903, 1999.

MediLink Technical Manual Version 1.5, Algotec, 2001.

VEPRO Computersysteme, MedImage: The Image Management System: DICOM Conformance Statement, Version 4.42, May 8, 2000.

MEDIMAGE Software Modules Brochure, pp. 1-9, Aug. 12, 1997.

ALGOTEC, MediPrime DICOM Conformance Statement, 2000.

ALGOTEC, MediStore Technical Manual Version 1.1, 1999.

MEDVISION, VisiTran-MD, Screen Captures, 1997.

Meeting Notes: XRE / Camtronics, 3 pages, 1998.

Mehta A et al., Enhancing Availability of the Electronic Image Record for Patients and Caregivers During Follow-Up Care, Journal of Digital Imaging, May 1999, pp. 78-80, vol. 12—No. 2—supp.1.

Merge Technologies, Inc., Connectivity Products: MergeArk, 1999.

Merge Technologies Inc., Setting the Course for Electronic Image Management, Feb. 1998.

Merge Technologies Inc., MergeWorks: Connect, 1997.

Merge Technologies Inc., MergeWorks: Datasheets, 1997.

Merge Technologies Inc., MergeWorks: Print, 1997.

Merge Technologies Inc., MergeWorks: Store, 1997.

Scism, KC, Letter from Kenneth C Scism (META Solutions, Inc.) to Robert Brannon (CMS Imaging Inc.) re enclosed literature briefs regarding META Solutions, Inc., the RadWorks portfolio, and a DICOM Conformance Statement of the RadWorks 2.1 Product Line and enclosures thereto, Jan. 19, 1998.

Torres MA et al., A Comprehensive Emergency Services Assessment, 1996 Annual HIMSS Conference and Exhibition.

Abiri M & Kirpekar N, Designing a Request for Proposal for Picture Archiving and Communication System, Journal of Digital Imaging, Aug. 1997, pp. 20-23, vol. 10—No. 3.

Longo MC & Lockhart P, Structured Cabling: Foundations for the Future, 1996 Annual HIMSS Conference and Exhibition.

Bettinger ME, Tracking Critical Patient Information With a Social Work Activity Database, 1996 Annual HIMSS Conference and Exhibition.

Bissell MG & Miller WE, Reengineering Laboratory Operations, 1996 Annual HIMSS Conference and Exhibition.

Cannavo MJ, Commentary: PACS and TeleRadiology: Who Pays the Bill?, Diagnostic Imaging, Sep. 1998, pp. P15-P17.

Cannavo MJ, PACS Integration: Info Network Integrates Islands of Automation, Diagnostic Imaging, Feb. 1998, pp. 25-27.

Hafner MJ, Effectiveness of Device Locations in the UIHC's Computerized Charting System, 1996 Annual HIMSS Conference and Exhibition.

DICOM Standards Committee, Working Group I (Cardiac and Vascular Information), Committee Minutes, Jan. 19-20, 1999.

DICOM Standards Committee, Working Group I (Cardiac and Vascular Information), Minutes, Jun. 22-23, 1999.

DICOM Standards Committee, Working Group 6 (Base Standard), Minutes, Jun. 28, 1999.

Curtis MS & Brown A, The Role of Information Systems in Medicaid Managed Care, 1996 Annual HIMSS Conference and Exhibition.

Ratib O et al., Multimedia image and data navigation workstation, RadioGraphics, Mar.-Apr. 1997, pp. 515-521, vol. 17—No. 2.
*Datcard v. Codonics* Civil Action No. SACV 08-00063 AHS, Notice of Manual Filing, filed Jan. 16, 2009.
*Datcard v. Codonics* Civil Action No. SACV 08-00063 AHS, Notice of Manual Filing, filed Jan. 26, 2009.
*Datcard v. Codonics* Civil Action No. SACV 08-00063 AHS, Notice of Motion to Compel Compliance with Subpoena to Rimage Corporation, dated Jan. 19, 2009.
*Datcard v. Codonics* Civil Action No. SACV 08-00063 AHS, Order Granting DatCard's Application for an Order to File the Declaration of A. Rosenzweig Under Seal, dated Jan. 20, 2009.
*Datcard v. Codonics* Civil Action No. SACV 08-00063 AHS, Order Granting Motion for Stay Pending Outcome of Reexamination of Patent-in-Suit, dated Feb. 3, 2009.
Order Granting Request for Ex Parte Reexamination of U.S. Patent No. 7,302,164, Control No. 90/009,347, Jan. 30, 2009.
Arri, Oscar: Optical system for cine archiving and review, Feb. 1999.
University Hospital of Geneva, OSIRIS Imaging Software User Manual, Version 3.1, 1996.
University Hospital of Geneva, OSIRIS Imaging Software Version 3.1 Packaging, 1996.
oTech news, 1997, pp. 1-4, vol. 2—iss.2.
Andriole KP et al., PACS Databases and Enrichment of the Folder Manager Concept, Journal of Digital Imaging, Feb. 2000, pp. 3-12, vol. 13—No. 1.
Horii SC, PACS mini refresher course: Electronic imaging workstations: Ergonomic issues and the user interface, RadioGraphics, Jul. 1992, pp. 773-787, vol. 12—No. 4.
Honeyman JC et al., PACS mini refresher course: Evaluation of requirements and planning for picture archiving and communication system, RadioGraphics, Jan. 1992, pp. 141-150, vol. 12—No. 1.
Frost MM et al., PACS mini refresher course: Image archival technologies, RadioGraphics, Mar. 1992, pp. 339-343, vol. 12—No. 2.
Bidgood WD & Horii SC, PACS mini refresher course: Introduction to the ACR-NEMA DICOM Standard, RadioGraphics, Mar. 1992, pp. 345-355, vol. 12—No. 2.
Stewart BK, PACS mini refresher course: Local area network topologies, media, and routing, RadioGraphics, May 1992, pp. 549-566, vol. 12—No. 3.
Horii SC & Bidgood WD, PACS mini refresher course: Network and ACR-NEMA DICOM protocols, RadioGaphics, May 1992, pp. 537-548, vol. 12—No. 3.
Choplin RH et al., PACS mini refresher course: Picture archiving and communication systems: An overview, RadioGraphics, Jan. 1992, pp. 127-129, vol. 12—No. 1.
Seshadri SB et al., PACS mini refresher course: Software suite for image archiving and retrieval, RadioGraphics Mar. 1992, pp. 357-363, vol. 12—No. 2.
Boehme II JM & Choplin RH, PACS mini refresher course: System integration: Requirements for a fully functioning electronic radiology department, RadioGraphics, Jul. 1992, pp. 789-794, vol. 12—No. 4.
Huang HK, PACS mini refresher course: Three methods of implementing a picture archiving and communication system, RadioGraphics, Jan. 1992, pp. 131-139, vol. 12—No. 1.
Dwyer SJ et al., PACS mini refresher course: Wide area network strategies for teleradiology system, RadioGraphics, May 1992, pp. 567-576, vol. 12—No. 3.
Huang HK, PACS: Picture archiving and communication systems in biomedical imaging, 1996, pp. 396-401 and Table of Contents.
Datcard Systems, PacsCube User Manual / Installation Guide Version 4.1, 2006, pp. 1-63.
Final Text—Supplement 3—Part 12, Digital Imaging and Communications in Medicine (DICOM), Part 12: Media Format and Physical Media for Media Interchange, Feb. 26, 1995.
Azmoun LM et al., Finding the path: A worldwide web-based guide for imaging evaluation of patients in the emergency department, RadioGraphics, Jan.-Feb. 1997, pp. 213-218, vol. 17—No. 1.
First DIN-PACS award goes to IBM as Computer Giant Wins Portsmouth Bid, DI Scan, Mar. 4, 1998, pp. 1-2.
Blaine GJ et al., Project Spectrum: Technology Alliance for the Emerging Integrated Health System, HIMSS Proceedings, 1996, pp. 260-270, vol. 2.
Gamerman GE, Development and Implementation Case Study: Clearing the Legal, Regulatory, and Contractual Barriers, HIMSS Proceedings, 1996, pp. 66-79, vol. 2.
Conrad GR, A Simple Image Display Application for Windows, Journal of Digital Imaging, Aug. 1997, pp. 115-119, vol. 10—No. 3.
GE Medical Systems, Technical Publications: Direction 09610-0025: Revision B: CRS-PC/CRS-PC+1.3 Conformance Statement for DICOM v3.0, 2000.
GE Medical Systems, Technical Publications: IIS FP10282: Revision 1: PathSpeed PACS Version 8.0 Conformance Statement for DICOM V3.0, Sep. 2000.
GE Medical Systems, Press Information: AmeriNet and GE Medical Systems Sign National Contract for Ultrasound Systems, Oct. 26, 1999.
GE Medical Systems, Press Information: GE Healthcare Financial Services Announces Innovative Online Offerings to Boost Hospital and Clinic Productivity, Nov. 28, 1999.
GE Medical Systems, Press Information: GE Increases Power of MR Imaging With New Gradient Platforms: New Gradients Deliver Power and Speed, Nov. 28, 1999.
GE Medical Systems, Press Information: GE Medical Brings Six Sigma Quality to Customers, Nov. 28, 1999.
GE Medical Systems, Press Information: GE Medical Systems Brings All-In-One Nuclear Cardiac Software to GE Workstations: 'Emory Cardiac Toolbox' Gives Physicians Greater Access to Patient Data, Nov. 28, 1999.
GE Medical Systems, Press Information: GE Medical Systems Demonstrates World-Wide CT System Featuring Premium GE Technology: GE CT/e System to Provide Doctors, Patients Around the World With Access to State-of-the-Art GE CT Imaging Equipment, Nov. 28, 1999.
GE Medical Systems, Press Information: GE Medical Systems' Digital Chest X-Ray System Increases Physician Productivity, Improves Speed of Exams, Nov. 28, 1999.
GE Medical Systems, Press Information: GE Medical Systems Expands CT HISPEED Product Line: Introduces Faster Scanner and Mobile System to Make State-of-the-Art CT Technology Product Line Even Stronger, Nov. 28, 1999.
GE Medical Systems, Press Information: GE Medical Systems Expands Mobile Offerings Through Cardiac MR Scanner: SIGNA CV/i Now Available in a Mobile Configuration, Oct. 18, 1999.
GE Medical Systems, Press Information: GE Medical Systems Expands Portfolio of Online Productivity Solutions Available to Health Care Providers, Nov. 28, 1999.
GE Medical Systems, Press Information: GE Medical Systems First to Introduce High Performance Cancer Detecting Scanner for Mobile Services: Mobile Leader Makes Popular 'PET' Imaging Technology Accessible to Doctors, Patients Globally, Nov. 28, 1999.
GE Medical Systems, Press Information: GE Medical Systems' Integrated Imaging Solutions Announces Advanced Analysis Capabilities on PATHSPEED, Nov. 28, 1999.
GE Medical Systems, Press Information: GE Medical Systems' Integrated Imaging Solutions Announces PATHSPEED Release 8.0, Nov. 28, 1999.
GE Medical Systems, Press Information: GE Medical Systems' Integrated Imaging Solutions Demonstrates Advanced Internet Imaging Technologies at RSNA 1999, Nov. 28, 1999.
GE Medical Systems, Press Information: GE Medical Systems' Integrated Imaging Solutions Introduces ADVANTAGE Workstation 4.0, Nov. 28, 1999.
GE Medical Systems, Press Information: GE Medical Systems Introduces Advanced Mammography System with New Patented GE X-Ray Tube: System Reduces Radiation Exposure by 40 Percent, Nov. 28, 1999.
GE Medical Systems, Press Information: GE Medical Systems Introduces Advanced Patient Imaging Archive System to Help Hospitals Go Digital: State-of-the Art System Archives Patient Data Immediately; Promotes Better Access to Health Care, Nov. 28, 1999.
GE Medical Systems, Press Information: GE Medical Systems Introduces Advanced 'Smart' Ultrasound System, Nov. 28, 1999.

GE Medical Systems, Press Information: GE Medical Systems Introduces First Medical Imaging Software to Let Doctors 'Drive Around' Inside Patient Anatomy: First Generation Interactive MRI Software Lets Doctors do Real-Time Studies as Patients Breathe and Move, Nov. 28, 1999.

GE Medical Systems, Press Information: GE Medical Systems Introduces MR Technology to Help Physicians Obtain Chemical Information From the Brain: New Information to Supplement MRI Images of Brain to Help Guide Biopsies, Nov. 28, 1999.

GE Medical Systems, Press Information: GE Medical Systems Introduces New Breakthrough Medical Imaging Procedure, Sep. 30, 1999.

GE Medical Systems, Press Information: GE Medical Systems Introduces New Tool to Aid in Minimally Invasive Surgeries, Nov. 28, 1999.

GE Medical Systems, Press Information: GE Medical Systems Introduces Revolutionary X-Ray Technology: GE Advantx LCA+ System Helps Treat Blood Vessel Diseases Linked to Heart Attacks and Strokes, Nov. 28, 1999.

GE Medical Systems, Press Information: GE Medical Systems Launches New Enterprise-Wide Services Offering for Health Care Providers: CompareCare to Promote Productivity and Simplification of Equipment Services Hospital-Wide, Nov. 28, 1999.

GE Medical Systems, Press Information: GE Medical Systems Makes New Advanced Ultrasound Systems Affordable for Smaller Hospitals and Clinics: Medical Profession Embraces GE's Development of High-Tech Systems, Nov. 28, 1999.

GE Medical Systems, Press Information: GE Medical Systems Provides Comprehensive Solutions to Help Health Care Providers Make Digital Transformation: GE's Full-Service Digital Solutions Promote Hospital-Wide Productivity, Patient Health Care Accessibility, Nov. 28, 1999.

GE Medical Systems, Press Information: GE Medical Systems Redesigns Customer-Driven Service Business for the New Millennium, Nov. 28, 1999.

GE Medical Systems, Press Information: GE Medical Systems Signs Five-Year Agreement With Navix Radiology Systems, Inc., Nov. 28, 1999.

GE Medical Systems, Press Information: GE Medical Systems Strengthens Commitment to Women's Health Care herSource Offerings: Global Leader in Health Care Services Provides More Solutions for Women's Health and Well-Being, Nov. 28, 1999.

GE Medical Systems, Press Information: GE Medical Systems Unveils New Biplane X-Ray System, Nov. 28, 1999.

GE Medical Systems, Press Information: GE Medical Systems Wins $1.4 Million Order to Provide State-of-the-Art Ultrasound Suite at Massachusetts General Hospital, Nov. 28, 1999.

GE Medical Systems, Press Information: GE Medical Systems' Integrated Imaging Solutions Announces PATHSPEED Prism: Software Integrates Patient Information in One Application, Nov. 28, 1999.

GE Medical Systems, Press Information: GE Medical Systems' Integrated Imaging Solutions Introduces PATHSPEED Extend, Nov. 28, 1999.

GE Medical Systems, Press Information: gemedicalsystems.com Offers New MR Technology for Sale Via Internet: Live Demonstrations to be Broadcast Daily from Radiology Community's Largest Trade Show, Nov. 28, 1999.

GE Medical Systems, Press Information: Introduction Accelerated by Six Sigma Quality: GE Introduces Breakthrough Ultrasound Technology; LOGIQ 700 Expert Series Offers Potential to Better Diagnose Stroke Risks, Apr. 29, 1999.

GE Medical Systems, Press Information: LIGHTSPEED QX/i: One Year Later: Breakthrough Multi-Slice CT Scanner Continues to Enhance Productivity Through New Technology, Improved Clinical Applications, Nov. 28, 1999.

GE Medical Systems, Press Information: New Volume Analysis Software From GE Medical Systems Allows Fast, Simple Analysis of Diagnostic Images on the GE Advantage Workstation, Nov. 28, 1999.

GE Medical Systems, Press Information: REVOLUTION XR/d Filmless X-Ray Table Enables Timely Patient Diagnosis and Treatment, Nov. 28, 1999.

GE Medical Systems, Press Information: Six Sigma Quality Design Leads to Faster Exams: GE Medical Systems Introduces Breakthrough 'Open' MRI System, Nov. 17, 1999.

GE Medical Systems, Press Information: Smaller Hospitals Get the Bigger Picture With GE Medical Systems' State-Of-The-Art Image Distribution System, Nov. 28, 1999.

GE Medical Systems, Radiological Society of North America, Press Information: Destination Digital, 1999.

Nussbaum GM, Protecting the Net: Leveraging the Infrastructure, HIMSS Proceedings, 1996, pp. 68-77, vol. 4.

Knight G, Project Management for Health Care Professionals, HIMSS Proceedings, 1996, pp. 342-352, vol. 1.

O'Neil GA & Uyeda K, Early Prototyping: Birth of an Ambulatory Care System User Interface, HIMSS Proceedings, 1996, pp. 280-292, vol. 2.

DR Systems, Inc., Guardian DICOM Archive Media Storage Conformance Statement, May 4, 1999.

Huang HK, PACS: Basic Principles and Applications, 1999, Wiley, New York.

U.S. Appl. No. 09/540,531, filed Mar. 31, 2000, Shoji et al.

U.S. Appl. No. 09/602,643, filed Jun. 22, 2000, Rothschild.

U.S. Appl. No. 11/740,062, filed Apr. 25, 2007, Canessa et al.

U.S. Appl. No. 60/181,215, filed Sep. 2, 2000, Segal.

U.S. Appl. No. 60/181,985, filed Feb. 11, 2000, Wright et al.

U.S. Appl. No. 60/205,751, filed May 19, 2000, Samari-Keirmani.

"PACS Market Moves at Brisk Pace as Interest in Technology Grows," PACS & Networking News, vol. 2, No. 5, pp. 1-3, dated May 1998.

"RSNA, HIMSS Join Forces to Sponsor Systems Integration," PACS & Networking News, vol. 2, No. 4, p. 1, dated Apr. 1998.

"Security, ASP, Systems Integration to Highlight PACS Exhibits (Agfa through Arnicas)," AuntMinnie.com, dated Nov. 26, 2000.

"Security, ASP, Systems Integration to Highlight PACS Exhibits (InSiteOne through Rogan)," AuntMinnie.com, dated Nov. 16, 2000.

Acuson Corp., "Acuson Introduces ViewPro-Net Network Image Review Software Package," PR Newswire, dated Mar. 8, 1999.

"Antelope Valley Hospital Chooses Algotec for Full PACS Installation; Major Los Angeles County Hospital has History of Technological Innovation," Business Wire, dated Nov. 28, 2000.

"DICOM—Digital Imaging and Communications in Medicine," Presentations of the European Society of Cardiology (ESC), dated Aug. 25, 1999.

"DICOM Standards Committee: writeable CD-ROMs May Become Gold Standard of Image Exchange," Non-invasive Imaging, dated Feb. 1999.

"Digital Imaging and Communications in Medicine (DICOM)," National Electrical Manufacturers Association, Copyright 1999.

"Image Workstation DICOM Conformance Statement," Camtronics Medical Systems, Copyright 1999.

"Med-volviz-faq-2000-01," dated Jan. 2000.

"Med-volviz-faq-98-11," dated Nov. 1998.

"New Products & Services: News Briefs," Health Management Technology, dated Feb. 1, 2000.

"New Solution Offers Film Copying to CD—View DICOM on Any PC," PR Newswire, dated Nov. 28, 2000.

"SPEC, DICOM Interface, TREXnet HR to IWS," Trex Medical Corp., 2 pages, dated 1999.

"SPEC, DICOM Interface, TREXnet HR to IWS," Trex. Medical Corp., 4 pages, dated 1999.

"SPEC, FUNC, TREXnet HR Image Network," Trex Medical Corp., 42 pages, revised Jan. 25, 2000.

"SPEC, FUNC, TREXnet HR, Phase I," Trex Medical Corp., 29 pages, revised Jan. 12, 1999.

"TDF Corporation Announces Statement of Direction to Integrate Image Edition with IBM ImagePlus VisualInfo," TDF Corporation, Apr. 1, 1996.

"TDK Launches Innovative Medical DVD/CD Recording Station With Embedded PC," redOrbit.com, dated Sep. 13, 2004.

"Three-In-One: Siemens' SIENET MagicView 300 PACS Software Offers Image Distribution, Teleradiology and Mini-Archive," PRNewswire, Jun. 11, Copyright 1996-2008.

Arenson RL & Friedenberg RM, 10th Conference on Computer Applications to Assist Radiology and 4th Conference on Computer Assisted Radiology, 1990, pp. 1-441, Symposium Foundation.

Arenson RL & Friedenberg RM, 10th Conference on Computer Applications to Assist Radiology and 4th Conference on Computer Assisted Radiology, 1990, pp. 442-791, Symposium Foundation.
Brody W & Johnston G, 11th Conference on Computer Applications in Radiology and 6th Conference on Computer assisted Radiology, 1992, pp. 1-376.
Brody W & Johnston G, 11th Conference on Computer Applications in Radiology and 6th Conference on Computer assisted Radiology, 1992, pp. 376-434, 445-749.
Boehme J & Rowberg A, 12th Conference on Computer Applications in Radiology and 8th Conference on Computer Assisted Radiology, Jun. 12-15, 1994.
Kilcoyne R et al., 13th Conference on Computer Applications in Radiology, Jun. 6-9, 1996.
HIMSS Conference and Exhibition, "Readme," 1996.
HIMSS Conference and Exhibition, Managing Care: The Race is On, dated Mar. 3-7, 1996 (reference provided in seven parts).
Flatau RJ, 510(k) summary: Cardiovascular Work Station (CWS) 5000 and CWS 3000, dated Oct. 7, 1999.
Carl FM et al., A five-step approach to digital image manipulation for the radiologist, Radiographics Jul.-Aug. 2002, pp. 981-992, vol. 22—No. 4.
Perry JH, A generic hospital PACS RFP presented to the Seventh RIS-PACS School, Georgetown University Medical Center, dated Jul. 9, 1997.
Dionisio J.D.N. et al., A Unified Timeline Model and User Interface for Multimedia Medical Databases, Computerized Medical Imaging and Graphics, Jul.-Aug. 1996, pp. 333-346, vol. 20—iss.4.
Ramaswamy M.R. et al., Computers in Radiology: Accessing Picture Archiving and Communication System Text and Image Information Through Personal Computers, AJR, Nov. 1994, pp. 1239-1243, vol. 163.
ACCUSOFT, High-Performance Medical Imaging Software (1997).
SIEMENS, Acom.Convert DICOM Conformance Statement, dated Sep. 15, 1999.
ACOM.PC 2.2 DICOM Conformance Statement, Version1.0, dated Sep. 29, 1999.
ACR Learning File Sampler 1 (32-bit), Help File, dated 1999.
Adobe, Adobe Opens the Digital Door to Visually Enhancing the Web with a Complete Family of Digital Imaging Products (Jun. 17, 1999).
Hilbel T. et al., Advantages of a Cardiac DICOM Network Server / Writer for Viewing and Permanent CD-R Archiving of Cardiovascular Angiography Images, Computers in Cardiology, 2000; pp. 649-652, vol. 27.
Advisory Action, U.S. Appl. No. 09/753,792, mailed Oct. 8, 2008.
Advisory Action, U.S. Appl. No. 09/761,795, mailed Jan. 16, 2007.
AGFA IMPAX Quotation, dated Jun. 8, 1998.
Aggarwal A. et al., "Predictors of Mortality and Resource Utilization in Cirrhotic Patients Admitted to the Medical ICU", Chest, May 5, 2001, pp. 1489-1497, vol. 119.
Mattheus R. et al. AIM: Advanced informatics in medicine, EurIPACS, European integrated picture archiving & communication system in the hospital, dated Dec. 31, 1994.
ALGOTEC Systems Ltd., From Board Design to Multi-Modality Workstations, dated Nov. 1994.
ALGOTECH, CDSurf, Help File, dated 1999.
ALGOTECH, CDSurf, Packaging, dated 1999.
American Society of Echocardiography, DICOM Demonstration, Toronto, Canada, dated Jun. 14-16, 1995.
Mehta A. et al., "Enhancing Availability of the Electronic Image Record for Patients and Caregivers During Follow-Up Care," Journal of Digital Imaging, May 1999, pp. 78-80, vol. 12—No. 2.
Wu T.-C. et al., An economical, personal computer-based picture archiving and communication system, Radiographics, Mar.-Apr. 1999, pp. 523-530, vol. 19—iss.2.
ANALOGIC, SuperDASM Configuration Keywords: A White Paper Engineering Document, Rev. 2, dated Jul. 13, 1998.
ESC Task Force on Digital Imaging, Becker T., Angiocardiography without cinefilm: information on the new digital imaging interchange standard for cardiology based on DICOM, last updated Jun. 11, 1996.
Valenta A. et al., "Informatics Education: Evolving Competencies, Continuing Discussions," HIMSS Proceedings, 1996, pp. 100-108, vol. 2.

APPLICARE Medical Imaging B.V., The RadWorks Product Line Version 2.1 Product Catalog (Summer 1997).
APPLICARE Medical Imaging B.V., The RadWorks Product Line (1997).
AREEDA Associates, "Welcome to the SeeMor Demo CD," dated 1999.
AREEDA Associates, SeeMor Medical Image Viewing Software for Windows 95/NT and Macintosh, "Readme.txt," dated Nov. 17, 1997.
AREEDA Associates, SeeMor Users Manual, dated 1997.
AREEDA Associates, SeeMor Version 3, "Apple Macintosh MacOS 8.x Users Manual," dated 1997.
AREEDA Associates, SeeMor Version 3, "Windows 9X/2000/NT4 Users Manual," dated 1999.
Scherpbier HJ et al., Aspects of Knowledge Sharing Using the Arden Syntax, HIMSS Proceedings, 1996, pp. 110-122, vol. 2.
McQueen, Jr HE Jr. & Manzone K, Enabling HMO Product Implementation Through Improved Work Processes and Technology, HIMSS Proceedings, 1996, pp. 252-258, vol. 1.
Haveri, M, Imedical Image Volume Visualization Software FAQ, Nov. 23, 1998.
Hipax Medical Imaging and Communication System Version 3 User Instruction Manual, Sep. 1999.
Osteaux M, Hospital integrated picture archiving and communication systems: A second generation PACS concept, 1992, Springer-Verlag, Berlin.
Huang HK, PACS: Basic Principles and Applications, 1999, pp. vii-xvii, 177-198, 284-288, 338-342, Wiley-Liss, Inc., USA.
Chin H et al, Digital Photography of Digital Imaging and Communication in Medicine—3 Images From Computers in the Radiologist's Office, Journal of Digital Imaging, May 1999, pp. 192-194, vol. 12—No. 2.
ICMIT, DICOM Development Project, Jun. 19, 1996.
ICMIT, DICOM Development Project: What is DICOM Anyway?, Dec. 18, 1995.
ICMIT, Patient Information Folder Project Demonstration, Sep. 11, 1996.
ICMIT, Patient Information Folder Project, Jul. 4, 1996.
Jaffe CC, Image archives and image data bases: How do they differ?, RadioGraphics, May 1994, p. 552, vol. 14—No. 3.
TFD Corp., Image Edition Product Webpage: The TDF Product Line, 1997.
IMAGEAXS, Pro-Med 4.01, Read Me, Aug. 20, 1998.
ALGOTEC Systems, Imaginet Product Brochure, 1998.
ALGOTEC Systems, ImagiNet Workflow and Management Manual Version 3.0, 2003.
Kodak Picture CD, Imaging Resource, http://www.imaging-resource.com/PRODS/PCD/PCDA.HTM, Nov. 10, 1999.
IMPAX Price Quotation for Laurie Imaging Center with annotations, Apr. 27, 1998.
IMPAX Web 1000 DICOM Web Server Specifications, May 30, 1998.
Hindel R, Implementation of the DICOM 3.0 Standard: A pragmatic handbook, 1994.
Prior FW, Information management and distribution in a medical picture archive and communication system, 1992.
Mammome GL et al., Inside BringhamRAD: Providing radiology teaching cases on the internet, RadioGraphics, Nov. 1995, pp. 1489-1498, vol. 15—No. 6.
Frank MS et al., Computers in Radiology: Integrating a Personal-Computer Local-Area Network with a Radiology Information System: Value as a Tool for Clinical Research, AJR, Mar. 1994, pp. 709-712, vol. 162.
Henderson M et al., Integrating the healthcare enterprise: A primer: Part 4. The role of existing standards in IHE, RadioGraphics, Nov.-Dec. 2001, pp. 1597-1603, vol. 21—No. 6.
Ticoll D, Interactive Multimedia in the High Performance Organization: Wealth Creation in the Digital Economy, 1995.
Kinsey TV, Interfacing the PACS and the HIS: Results of a 5-year Implementation, RadioGraphics, May-Jun. 2000; pp. 883-891, vol. 20—No. 3.
Invoice from Impax Technology to Agfa Inc. (CAN), Nov. 30, 2000.
Invoice from Impax Technology to Toshiba America, Inc., Jan. 31, 2000.

Invoice from Mitra Imaging to Agfa Division of Bayer Inc., Oct. 18, 1998.
Invoice from Mitra Imaging to EMED, Sep. 30, 1996.
Invoice from Mitra Imaging to Fuji Medical Systems, U.S.A., Mar. 24, 1997.
Invoice from Mitra Imaging to Siemens Health Services, Mar. 11, 1998.
Invoices and Sales Orders from Mitra Imaging to Picker International, Jun. 16, 1999.
Invoices from Impax Technology to Agfa Corporation, from Mar. 1, 2000 to Jan. 10, 2001.
Invoices from Impax Technology to Agfa Europe, from Nov. 3, 2000 to Jan. 15, 2001.
Invoices from Impax Technology to Agfa Hong Kong Ltd., from Jun. 21, 2000 to Aug. 22, 2000.
Invoices from Impax Technology to Agfa-Gevaert Ltd. (AUS), from Aug. 25, 2000 to Nov. 28, 2000.
Invoices from Impax Technology to Toshiba Corporation, from Oct. 25, 2000 to Jan. 16, 2001.
Invoices from Mitra Imaging to Acuson Corp., from Oct. 5, 1997 to Jan. 31, 2000.
Invoices from Mitra Imaging to Agfa Gevaert N.V., from Oct. 28, 1997 to Mar. 16, 2000.
Invoices from Mitra Imaging to Impax Technology, from Jul. 31, 1999 to Dec. 31, 2000.
Ackerman LV, infoRAD: Informatics in Radiology: A look at infoRAD 1992, RadioGraphics, Sep. 1992, pp. 979-980, vol. 12—No. 5.
Schwartz LH & Lossef SV, A low-cost CD-ROM based image archival system, RadioGraphics Jan. 1995, pp. 151-154, vol. 15—No. 1.
Stahl JN et al., A new approach to teleconferencing with intravascular US and cardiac angiography in a low-bandwidth environment, RadioGraphics, Sep.-Oct. 2000, pp. 1495-1503, vol. 20—No. 5.
Perry JH, A PACS RFP toolkit presented to The Fifth RIS-PACS School, Georgetown University Medical Center, Feb. 3, 1995.
Perry JH, A PACS RFP toolkit presented to the Seventh RIS-PACS School, Georgetown University Medical Center, Aug. 11, 1997.
AREEDA Associates, SeeMor, Demo CD ReadMe.txt File, Nov. 11, 1999.
Levy AL et al., An Internet-Connected, Patient-Specific, Deformable Brain Atlas Integrated into a Surgical Navigation System, Journal of Digital Imaging, Aug. 1997, pp. 231-237, vol. 10—No. 3.
ARRI, ARRI Oscar Product Brochure, 1999.
Salvekar AM et al., Community-Wide Implementation of Quality Outcome Measurements and Patient Satisfaction Report, 1996 Annual HIMSS Conference and Exhibition.
Kumar AP et al., Transforming Organization Structures to Implement Integrated Delivery Systems, 1996 Annual HIMSS Conference and Exhibition.
Atsutoshi O et al., Interhospital Network System Using the Worldwide Web and the Common Gateway Interface, Journal of Digital Imaging, May 1999, pp. 205-207, vol. 12—No. 2.
King, Jr. BF, Conversion Process: Calculates Film Costs Before Going Electronic, Diagnostic Imaging, Sep. 1997, pp. P47-P50.
Hersher BS et al., The CIO's Position in Today's Emerging Health Care System: Lessons Learned, 1996 Annual HIMSS Conference and Exhibition.
Bills of Lading, Invoices, and Packing Lists from Mitra Imaging to Institute de Cardiology de Montreal, dated May 1, 1998.
Erickson BJ et al., READS: A Radiology-Oriented Electronic Analysis and Display Station, Journal of Digital Imaging, Aug. 1997, pp. 67-69, vol. 10—No. 3.
Paige BM, Information Warehousing in the Integrated Delivery System, 1996 Annual HIMSS Conference and Exhibition.
Hard R, Brigham and Women's teams PACS, RIS technologies—Brigham and Women's Hospital in Boston combines Picture Archival Communication Systems and radiology information systems technologies—includes related article on imaging technology trends, Mar. 1994.
Business Profile of Algotec: Where the Web PACS the punch, Jun. 22, 2000.
Henri CJ et al., Evolution of a Filmless Digital Imaging and Communications in Medicine—Conformant Picture Archiving and Communications System: Design Issues and Lessons Learned Over the Last 3 Years, Journal of Digital Imaging, May 1999, pp. 178-180, vol. 12—No. 2.
Camtronics Medical Systems, Service Manual Image Workstation Series, 1999.
Camtronics, Ltd., Camtronics Medical Systems: Image Workstation: DICOM Conformance Statement: Document No. 09610-0021 (Rev. A), Oct. 26, 1999.
Eastman Kodak Co., Cardiology Products Webpage, 1997.
Boston C & Diedling L, Clinical Process Reengineering: Process, Potential and Pitfalls, 1996 Annual HIMSS Conference and Exhibition.
CD-R & CD-RW: Questions and Answers, OSTA Optical Storage Technology Association, dated Jul. 15, 1997.
ALGOTEC, CD-Surf User's Guide Version 1.0, 2001.
*Datcard* v. *Codonics* Civil Action No. SACS 08-00063 AHS, Certified Transcript of Non-Confidential Portions of Jan. 13, 2009 Deposition of Kenneth L. Wright, including Exhibits (Nos. 23 and 24) thereto.
Smith CN, Staffing and Patient Classification in a Post Anesthesia Care Unit, 1996 Annual HIMSS Conference and Exhibition.
Spurr CD et al., Automating Critical Pathways—One Hospital's Experience, 1996 Annual HIMSS Conference and Exhibition.
McDonald CJ, Implementing a Physician Order Entry System: Perspectives From Five Physicians, 1996 Annual HIMSS Conference and Exhibition.
Kundel HL, Clinical Experience with PACS at the University of Pennsylvania, Computerized Medical Imaging and Graphics, May-Jun. 1991, vol. 15—No. 2.
Medical Advanced Technology Management Office, Medical Research and Material Command, Clinical experience with PACS, presented at the Radiological Society of North America 81st Scientific Assembly and Annual Meeting, Nov. 25-Dec. 1, 1995.
*Datcard* v. *Codonics* Civil Action No. SACV 08-00063 AHS, Codonics, Inc.'s Answer and Defenses to DatCard Systems' Complaint and Counterclaims, filed Mar. 4, 2008.
*Datcard* v. *Codonics* Civil Action No. SACV 08-00063 AHS, Codonics, Inc.'s First Set of Requests for Production of Documents and Things, dated Jun. 6, 2008.
*Datcard* v. *Codonics* Civil Action No. SACV 08-00063 AHS, Codonics, Inc.'s Initial Invalidity Contentions and Initial Non-Infringement Contentions, dated Oct. 31, 2008.
*Datcard* v. *Codonics* Civil Action No. SACV 08-00063 AHS, Codonics, Inc.'s Memorandum in Support of Motion and Motion for Stay Pending Reexamination of the Patent-in-Suit, filed Dec. 29, 2009.
*Datcard* v. *Codonics* Civil Action No. SACV 08-00063 AHS, Codonics, Inc.'s Memorandum of Points and Authorities in Support of Motion for Stay Pending Reexamination of the Patent-in-Suit, filed Dec. 12, 2008.
*Datcard* v. *Codonics* Civil Action No. SACV 08-00063 AHS, Codonics, Inc.'s Notice of Motion and Motion for Stay Pending Reexamination of the Patent-in-Suit, filed Dec. 29, 2008.
*Datcard* v. *Codonics* Civil Action No. SACV 08-00063 AHS, Codonics, Inc.'s Objections and Responses to DatCard Systems, Inc.'s Fourth Set of Requests for Production of Documents and Things (Nos. 112-225), dated Jan. 26, 2009.
*Datcard* v. *Codonics* Civil Action No. SACV 08-00063 AHS, Codonics, Inc.'s Objections and Responses to DatCard Systems, Inc.'s Second Set of Requests for Production of Documents and Things (Nos. 44-78), dated Nov. 21, 2008.
*Datcard* v. *Codonics* Civil Action No. SACV 08-00063 AHS, Codonics, Inc.'s Objections and Responses to DatCard Systems, Inc.'s Third Set of Interrogatories (No. 12), dated Jan. 20, 2009.
*Datcard* v. *Codonics* Civil Action No. SACV 08-00063 AHS, Codonics, Inc.'s Objections and Responses to DatCard Systems, Inc.'s Third Set of Requests for Production of Documents and Things (Nos. 79-111), dated Dec. 19, 2008.
*Datcard* v. *Codonics* Civil Action No. SACV 08-00063 AHS, Codonics, Inc.'s Response to DatCard Systems, Inc.'s First Set of Requests for Production of Documents and Things (Nos. 1-43), dated Jun. 3, 2008.

*Datcard v. Codonics* Civil Action No. SACV 08-00063 AHS, Codonics, Inc.'s Response to DatCard's First Set of Interrogatories (Nos. 1-8), dated Jun. 3, 2008.
*Datcard v. Codonics* Civil Action No. SACV 08-00063 AHS, Codonics, Inc.'s Second Set of Requests for Production of Documents and Things (Nos. 84-195), dated Dec. 5, 2008.
*Datcard v. Codonics* Civil Action No. SACV 08-00063 AHS, Codonics, Inc.'s Supplemental Responses to DatCard's First Set of Interrogatories (Nos. 1-8), dated Nov. 6, 2008.
*Datcard v. Codonics* Civil Action No. SACV 08-00063 AHS, Codonics' Reply in Support of Motion for Stay Pending Reexamination of the Patent-in-Suit, filed Jan. 26, 2009.
Prophet CM et al., On the 'Paperless Trail'—A Computerized Charting System, 1996 Annual HIMSS Conference and Exhibition.
TREX Medical Corp., Company Overview Webpage, dated 2008.
Binet EF et al., Computer-based radiology information system: From floppy disk to CD-ROM, RadioGraphics, Sep. 1995, pp. 1203-1214, vol. 15—No. 5.
Varma DGK et al, Computerized scientific exhibit in radiology: A valuable format for delivering scientific information, RadioGraphics, Sep. 1994, pp. 1127-1138, vol. 14—No. 5.
Lee S-K et al., Consulting with radiologists outside the hospital by using Java, RadioGraphics, Jul.-Aug. 1999, pp. 1069-1075, vol. 19—No. 4.
Cooper T, Kaiser Permanente Anticipates High Costs as it Gears Up for HIPPA, IT Heath Care Strategist, Oct. 1999, p. 4, vol. 1—No. 10.
Corrected Original Request for Ex Parte Reexamination of U.S. Patent No. 7,302,164, Control No. 90/009,538, mailed Sep. 25, 2009.
Kolodny GM et al., Cost Savings in a Digital Radiology Department, RSNA EJ, 1997, vol. 1.
GE Medical Systems, CRS-PC / CRS-PC+ 1.3 Conformance Statement for DICOM V3.0, 2000.
McKinney C & Brockhaus S, Benefits of Cost Accounting Within a Multihospital System, HIMSS Proceedings, 1996, pp. 142-156, vol. 4.
McKinney C et al., Simplifying the Approach to Productivity Monitoring, HIMSS Proceedings, 1996, pp. 362-366, vol. 2.
Farber D et al., Camtronics IWS Open Issues List, updated Aug. 26, 1999.
Schultz DG, Letter re 510(k) Notification, Dec. 21, 1999.
Hanlon WB et al., Data storage and management requirements for the multimedia computer-based patient medical record, Fourteenth IEEE Symposium on Mass Storage Systems, pp. 11-16, 1995.
*Datcard v. Codonics* Civil Action No. SACV 08-00063 AHS, DatCard Systems, Inc.'s Complaint for Patent Infringement and Demand for Jury Trial, filed Jan. 18, 2008.
*Datcard v. Codonics* Civil Action No. SACV 08-00063 AHS, DatCard Systems, Inc.'s First Amended Initial Disclosures, dated Jul. 21, 2008.
*Datcard v. Codonics* Civil Action No. SACV 08-00063 AHS, DatCard Systems, Inc.'s Initial Disclosures, dated Apr. 16, 2008.
*Datcard v. Codonics* Civil Action No. SACV 08-00063 AHS, DatCard Systems, Inc.'s Reply to Codonics, Inc.'s Counterclaim, filed Mar. 13, 2008.
*Datcard v. Codonics* Civil Action No. SACV 08-00063 AHS, DatCard Systems, Inc.'s Response to Codonics, Inc.'s First Set of Requests for Production of Documents and Things (Nos. 1-83), dated Jul. 25, 2008.
*Datcard v. Codonics* Civil Action No. SACV 08-00063 AHS, DatCard Systems, Inc.'s Response to Codonics, Inc.'s Second Set of Requests for Production of Documents and Things (Nos. 84-195), dated Jan. 5, 2009.
*Datcard v. Codonics* Civil Action No. SACV 08-00063 AHS , DatCard Systems, Inc.'s Second Amended Initial Disclosures, dated Jan. 23, 2009.
*Datcard v. Codonics* Civil Action No. SACV 08-00063 AHS, DatCard's Application for an Order to File the Declaration of A. Rosenzweig Under Seal, filed Jan. 20, 2009.
*Datcard v. Codonics* Civil Action No. SACV 08-00063 AHS, DatCard's Opposition to Codonics' Motion for Stay Pending Codonics' Ungranted Request for Reexamination of the Patent-in-Suit, filed Jan. 16, 2009.

Niemeyer D et al. The Good, The Bad and The Usable—A Clinical Workstation, HIMSS Proceedings, 1996, pp. 1-10, vol. 4.
Avrin D, Radiology into the 21st Century: The Digital Department, Sep. 8-10, 1999.
Kimball DL, The Information Technology Leader's Role in Renewing the Healthcare Enterprise, HIMSS Proceedings, 1996, pp. 38-49, vol. 3.
Invoices, Sales Orders, and Packing Lists from Mitra Imaging to Agfa Corporation, dated Nov. 24, 1999.
Invoices, Sales Orders, Packing Lists, FexEd Manifests, and Billing Summaries from Mitra Imaging to Electromed International, dated from Sep. 5, 1997 to Sep. 20, 2000.
Klimczak JC & Bopp K, Reengineering Medical Records With a Text Archive and Retrieval System, HIMSS Proceedings, 1996, pp. 64-76, vol. 3.
Eisenman JI, Book Review—PACS Basic Principles and Applications, Radiology, Jul. 1999, p. 202.
Kohli J et al., Distributed Architecture for a Wide-Area Medical Image Repository, HIMSS Proceedings, 1996, pp. 190-200, vol. 1.
Brice J, Cover Story: In Search of Smart & Simple PACS Workstations, Diagnostic Imaging, Mar. 1998, pp. 42-46.
Brice J, PACS Integration: Radiology's Portal to Both Magic and Misery, Diagnostic Imaging, Sep. 1998, pp. P30-P42.
Benneyan JC, Improving Health Care Using SPC and Quality Engineering: Billing and Laboratory Case Studies, HIMSS Proceedings, 1996, pp. 32-40, vol. 2.
Thomas JD & Nissen SE, Digital Storage and Transmission of Cardiovascular Images: What are the Costs, Benefits and Timetable for Conversion?, Heart, 1996, pp. 13-17, 1996, vol. 76.
Thomas JD, Digital Storage and Retrieval: The Future in EchoCardiography, Heart, 1997, pp. 19-22, vol. 78.
Farstad JE et al., Operations, Facilities and Communications: Understanding Success Factors in Patient-Centered Care, HIMSS Proceedings, 1996, pp. 80-89, vol. 4.
Kazmer J et al., The Creation of a Virtual Electronic Medical Record, HIMSS Proceedings, 1996, pp. 150-162, vol. 2.
Lear JL, Redundant Array of Independent Disks: Practical On-Line Archiving of Nuclear Medicine Image Data, Journal of Digital Imaging, Feb. 1996, pp. 37-38, vol. 9—No. 1.
Smith JL, III et al., Laboratory Redesign: Life After Cap Units, HIMSS Proceedings, 1996, pp. 384-406, vol. 2.
Prescott JR, What's the Score and How Much Time is Left?, HIMSS Proceedings, 1996, pp. 328-333, vol. 2.
Wu JB et al., Wireless Data Transmission: How to Implement Remote Data-Access, HIMSS Proceedings, 1996, pp. 176-187, vol. 2.
Larson JA, The Reengineering Approach—Techniques and Tools, HIMSS Proceedings, 1996, pp. 360-373, vol. 1.
Oberson J-C et al., Development of an Electronic Radiologist's Office in a Private Institute, Radiographics, 2000, pp. 573-580, vol. 20.
Blair JS, An Overview of Health Care Information Standards, HIMSS Proceedings, 1996, pp. 202-212, vol. 1.
Muscarella JW & Hoben J, Delivering Information Services Via the World Wide Web, HIMSS Proceedings, 1996, pp. 102-112, vol. 4.
Mathis JL et al., Case Study: A Health Care System's Use of Wireless Technology, HIMSS Proceedings, 1996, pp. 90-97, vol. 2.
Hayes JC, Imaging News: Data Shows Filmless Imaging Saves in High-Volume Setting, Diagnostic Imaging, pp. 9-13, dated Jul. 1998.
Morgan JD et al., Building an Information Infrastructure: Practical Lessons From Three Multifacility Health Care Enterprises, HIMSS Proceedings, 1996, pp. 24-33, vol. 1.
Glaser J & Kuperman G, MD, PhD, Impact of Information Events on Medical Care, HIMSS Proceedings, 1996, pp. 2-9, vol. 2.
Lynch J, Chins: A Collaborative Approach to Outcomes Analysis, HIMSS Proceedings, 1996, pp. 20-29, vol. 2.
Kludt JR et al., Rebounding From Rejection: Reintroducing Physicians to Your IS, HIMSS Proceedings, 1996, pp. 92-99, vol. 4.
Cirillo JA & Wise LA, Testing the Impact of Change Using Simulation, HIMSS Proceedings, 1996, pp. 52-64, vol. 2.
Hennessey JG et al., Digital Video Applications in Radiologic Education: Theory, Technique, and Applications, Journal of Digital Imaging, May 1994, pp. 85-90, vol. 7—No. 2.

Hager J & Hartless C, Reengineering Laboratory Operations, HIMSS Proceedings, 1996, pp. 220-226, vol. 3.

Steinhart M, Declaration in Support of Request for Reexamination of U.S. Patent No. 7,302,164, Jun. 10, 2009.

Faulkner K, Book Review—PACS Basic Principles and Applications, The British Journal of Radiology, Jul. 1999, p. 690.

Hartmann-Voss K et al., Integrating Clinical Decision Support Technology to Existing Hospital Information Systems, HIMSS Proceedings, 1996, pp. 114-122, vol. 4.

Kincade K, Digital Processing: Wavelets Challenge JPEG in Image Compression, Diagnostic Imaging, Nov. 1997, pp. 125-127.

KBMC Productions, CDRS-1100AUTOTP Operator's Manual, Revision 1.2, 2002.

Weiner K & Levesque GE, This Hospital's Like a Hotel!, HIMSS Proceedings, 1996, pp. 44-54, vol. 4.

Dombkowski KJ et al., Using Electronic Data Interchange in Managed Care Performance Measurement, HIMSS Proceedings, 1996, pp. 160-176, vol. 1.

Verhoeven L & Mast EG, Coronary X-ray Angiography: 40 Years of Experience, MedicaMundi, Sep. 1999, pp. 48-54, vol. 43—iss.2.

Bain L et al., The Benefits and Implications of a Statewide Health Information Network for a Major Medical Center, HIMSS Proceedings, 1996, pp. 222-230, vol. 2.

Mantelman L, TDF Launches ImageMail—A 'Fed.EXE' for Digital Documents, ;Magazine, Nov. 1996.

Kennedy RL, Legacy System Integration Using Web Technology, Proc. of SPIE, Feb. 2000, pp. 231-234, vol. 3980.

Wise LA & Mermelstein PD, A Managed Care Demand Model for Ambulatory Care Services, HIMSS Proceedings, 1996, pp. 78-88, vol. 3.

Scholten LA and Hubble JC, Automated Nursing Supply Stations—Gold Mine or Fool's Gold, HIMSS Proceedings, 1996, pp. 312-329, vol. 1.

Hofmann J, Letter re MedImage—Digital Image and Document Management, 3 pages, Dec. 15, 1997.

Hein L, Letter re: *Datcard Systems, Inc.* v. *Codonics, Inc.*, Jan. 15, 2009.

Nikolai P, Letter re: *Datcard Systems, Inc.* v. *Codonics, Inc.*, Jan. 20, 2009.

Watson T, Letter from T. Watson (Algotech) to M. Cannavo (Image Management Consultants), Apr. 8, 1998.

Yin L, Letter re: 510(k) Notification, Nov. 19, 1997.

Keska LA, Letter re: Presentations, Oct. 1, 1999.

Nice LL and Archual GM, A Team Uses Simulation and Benchmarking to Improve Radiology Performance, HIMSS Proceedings, 1996, pp. 246-258, vol. 2.

Linda Reeder, Linking Outcomes—Based Documentation and Clinical Pathways With Automated Functions, HIMSS Proceedings, 1996, pp. 304-309, vol. 2.

Lockheed Martin, Operating Instructions, Vantage Picture Archiving and Communication System, 5.0 Release, Aug. 1996.

Molfetas L, Strategic CPR Issues: Benchmarking Paper Documentation Prior to Implementation, HIMSS Proceedings, 1996, pp. 56-69, vol. 1.

Desrosiers M, Abstract: The Multimedia CD ROM: An Innovative Teaching Tool for Endoscopic Sinus Surgery, J Laparoendosc Adv. Surg. Tech. A, Aug. 1998, pp. 219-224, vol. 8—iss.4.

Asadi MJ & Baltz WA, Clinical Pathways Costing: The Key to Profitability—An Example to Improve Cost and Efficiency Using Activity-Based Costing, HIMSS Proceedings, 1996, pp. 56-65, vol. 4.

Kaiser MA et al., New Information Requirements for the New World of Managed Health Care, HIMSS Proceedings, 1996, pp. 41-50, vol. 2.

510(k) Premarket Notification Database: Vepro Computersysteme GmbH, MedImage (K972215), MDRWeb.com, 2005.

MITRA Imaging, Inc., 510(k) Summary of Safety and Effectiveness (K974102), Jan. 20, 1998.

*Datcard* v. *Codonics* Civil Action No. SACV 08-00063 AHS, Codonics, Inc.'s Notice of Motion and Motion for Stay Pending Reexamination of the Patent-in-Suit, Dec. 12, 2008.

Dimitroff DC & Chang IF, An Object Oriented Approach to Automating Patient Medical Records, Proceedings of the 14th Annual International Computer Software and Applications Conference (COMPSAC), Oct. 31-Nov. 2, 1990, pp. 82-87.

Schildkamp DE & Callahan JA, OR Team Learns While Improving Stock and Reprocessing Workflow, HIMSS Proceedings, 1996, pp. 260-277, vol. 1.

Erbel R et al., Digital archiving of imaged heart catheter studies on CD-R: Detection of irreversible CD damage (Abstract), Herz., Dec. 1998, pp. 526-529, vol. 23—iss.8.

Kocna P., Digitalization, archival storage and use of image documentation in the GastroBase-II system, Cas Lek Desk., May 1997, pp. 311-314, vol. 136—iss.10.

Loomis C, Email from C Loomis (Camtronics) to R Desroches (XRE) re Direct Connect Workstations, Dec. 30, 1999.

Desroches R, Email from R Desroches (XRE) to L Ford (Camtronics) re Workstation Training, Jan. 19, 2000.

Paré G et al, Evaluating PACS Success: A Multidimensional Model, Proceedings of the 38th Hawaii International Conference on System Science, 2005, pp. 1-9.

Korn F et al., Fast nearest neighbor search in medical image databases, Proceedings of the 32nd VLDB Conference, 1996, pp. 1-12.

GE Medical Systems, Technical Publications: 2246811-100, rev. 2: Senographe 2000 D Review WorkStation: Conformance Statement for DICOM V3.0, 2003.

GE Medical Systems, GE Press Info—Radiological Society of North America, Images, 1999 (submitted in 2 parts).

Hanlon WB et al., Data Storage and Management Requirements for the Multimedia Computer-based Patient Medical Record, Proceedings of the Fourteenth IEEE Symposium on Mass Storage Systems, Sep. 11-14, 1995, pp. 11-16.

Haufe G et al., PACS at work: A Multimedia E-Mail Tool for the Integration of Images, Voice and Dynamic Annotation, Computer Assisted Radiology, 1996, pp. 417-419.

Hilbel T et al., Advantages of a Cardiac DICOM Network Server/Writer for Viewing and Permanent CD-R Archiving of Cardiovascular X-Ray Angiography Images, Computers in Cardiology, 2000, pp. 649-652, vol. 27.

Centura Health, Invoice and Check from Centura Health to VEPRO, Oct. 1, 1999.

Kleinholz L. et al.,Multimedia and PACS. Setting the Platform for Improved and New Medical Services in Hospitals and Regions, Computer Assisted Radiology, Jun. 1996, pp. 313-322.

May T, Medical Information Security: The Evolving Challenge, Proceedings of the 32nd Annual International Carnahan Conference on Security Technology, Oct. 1998, pp. 85-92.

Medweb, Medweb Image Server DICOM Conformance Statement, rev. 2.1, Jul. 1, 1998.

*Datcard* v. *Codonics* Civil Action No. SACV 08-00063 AHS, Minute Order (1) Taking Under Submission Defendant's Motion for Stay Pending Reexamination of the Patent-in-Suit; and (2) Removing the Matter From the Court's Feb. 2, 2009 Calendar, Jan. 27, 2009.

Channin DS et al., North by Northwestern: Initial Experience with PACS at Northwestern Memorial Hospital, Proceedings of SPIE, Feb. 2000, pp. 275-280, vol. 3980.

Huang HK, PACS Implementation Experiences: From In-house to Partnership to Advisory Board, Proceedings of SPIE, Feb. 2000, vol. 3980.

Huang HK, PACS: Picture archiving and communication systems, 1999.

Algotec, CD-Surf, Jan. 2, 2001.

Ando Y. et al., Clinical Application Of A Magneto-Optical Disk Image Filing System: A Prototype Of CT Image Magement System, 1991, IEEE.

Borderless Teleradiology with Chili, Engelmann et al., Journal of Medical Internet Research, Copyright 1999 [Retrieved from http://www.jmir.org/1999/2/e8, on Mar. 3, 2008].

Condit et al., Requirements for cardiac interchange media and the role of recorable CD, International Journal of Cardiac Imaging, 1995, pp. 153-157, vol. 11-supp.3.

Cox R.D. et al., DICOM-compliant PACS with CD-based image archival, SPIE, 1998, pp. 135-142, vol. 3339.

Cusma J.T. et al., Replacement of cinefilm with a digital archive and review network, International Journal of Cardiac Imaging, 1998, pp. 293-300, vol. 14.

Oberson J.-C. et al., Development of an electronic radiologist's office in a private institute, Radiographics, 2000, pp. 573-580, vol. 20-No. 2.
Medweb, Dicom Cube Internet Website, Jan. 2, 2001.
Etiam, DICOM 3.0 Conformance Statement: DICOM Eye v2.42 Version 1, Sep. 12, 2000.
ImageAXS Pro-Med Windows User's Guide, Digital Arts and Science, Alameda, CA, "Printed May 1998" (submitted in four parts).
Kaminsky et al, "Exchange of medical images via an universal magneto-optical disc interface", 1999.
Ligier et al., Echange de dossiers d'imagerie du patient sur CD-ROM compatible DICOM Informatique et santé, 2000 (12):241-248 Springer-Verlag France.
Medimage ACOM.Convert DICOM Archiving & Viewing Station Software Vers. 4.42 User Manual, Sep. 5, 1999 (66 pages).
MergeWorks: A system of flexible building blocks that provide DICOM infrastructure for electronic image management, MergeTechnologies, Inc., "webarchive.org" date "Dec. 2, 1998.".
Ohyama, "ISAC (Image Save and Carry) Standardization", Imaging Science and Engineering Laboratory Tokyo Inst. of Tech. 4259, Nagatsuta, Midori-ku, Yokohama,227 Japan, Copyright IEEE 1999.
Okano et al, "Digital image in cardiology now and for the future", Int J Card Imaging, 1998.
Okura, et al., Methods for efficient compressing and archiving medical digital motion images, Medical Imaging 2000: PACS Design and Evaluation: Engineering and Clinical Issues, Proceedings of SPIE, 2000, vol. 3980, pp. 7.
Wear P.K. et al., "Building Security Models for Patient Identifiable Health Information," 1996 Annual HIMSS Conference and Exhibition.
Horii S.C., Part four: A nontechnical introduction to DICOM, Radiographics 17:5, Sep.-Oct. 1997.
Internet website: PacsCube Solution: The PacsCube Software Solution Package Features, Jan. 2, 2001.
Payment from Siemens Nixdorf to Mitra Imaging, dated Apr. 9, 1998.
Payments from AGFA Corporation to Impax Technology, dated from Nov. 22, 2000 to Dec. 29, 2000.
Zimmerman R.E., Personal Notes: SNM 96: Jun. 1, 1996 to Jun. 6, 1996, dated Mar. 9 2009.
Katz P.A., Improving Competitive Position by Use of the Computerized Patient Record and Associated Technologies, 1996 Annual HIMSS Conference and Exhibition.
Drew P.G., Ph.D., "Signal-to-Noise: Surveys Attest to Growing Interest in PACS," Diagnostic Imaging, pp. 21-22, Jan. 1998.
Philips Medical Systems, 510(k) Summary for Philips Inturis DICOM Recorder (K993227), dated Dec. 21, 1999.
Philips Medical Systems, DICOM Conformance Statement: CD-Medical Recorder for DCI Systems CDM 3300: Release 1.1, Oct. 31, 1996.
Osteaux M. et al., Picture Archiving and Communication System (PACS): a Progressive Approach with Small Systems, European Journal of Radiology, 1996, pp. 166-174, vol. 22.
Huang H.K. et al., Picture Archiving and Communication Systems (PACS) in Medicine, 1991.
Pre-Production Release Form MQF-9.3 re: Project AS300, Version 4.5.0 from Mitra Imaging to Electromed International, Nov. 9, 1999.
Printed Screen Shots and Help File Topics of Exhibit 382 to the Deposition of Stefan Delank, dated Jan. 30, 2009, *Datcard Systems, Inc.* v. *Codonics, Inc.*, Civil Action No. SACV08-00063 AHS (RNBx), U.S. District Court, Central District of California (Vepro Demonstration CD, © 1996-1999).
Sorna Corp., Product Showcase: Automated DICOM Exchange Station, Medical Imaging Magazine, Jan. 2000, p. 72, vol. 15-No. 1.
Mun S.K., Ph.D., Project DEPRAD (Deployable Radiology and Teleradiology System) in Bosnia/Hungary, 1997.
Algotec, ProVision Product Brochure, 1996.
Purchase Order from Acuson Corp. to Mitra Imaging, dated Apr. 30, 1997.
Purchase Order, Invoice, Packing Slip, Billing Statement, Work Order from Mitra Imaging to Electromed Imaging and Mitra History dated Sep. 5, 1997 to Sep. 20, 2000.
Purchase Orders from Agfa Division to Mitra Imaging, dated from Apr. 30, 1999 to Oct. 14, 1999.
Purchase Orders from Electromed International to Mitra Imaging, dated from Apr. 29, 1998 to Jan. 9, 2000.
Purchase Requisitions from Electromed International to Mitra Imaging, dated May 1, 1998.
Davenport R.L. et al., "Understanding and Assessing CHIN Network Technology," 1996 Annual HIMSS Conference and Exhibition.
Cox R.D. et al., "Transparent Image Access in a Distributed Picture Archiving and Communications System: The Master Database Broker," Journal of Digital Imaging, May 1999, pp. 175-177, vol. 12-No. 2.
Ackerman L.V., Radiology and computer science, Radiographics, Nov. 1991, pp. 1027-1028, vol. 11-No. 6.
Radiology Service Partners, LLC, Re-Engineering Radiology, 1997.
Baxter A.B. et al., RadNotes: A novel software development tool for radiology education, Radiographics, May-Jun. 1997, vol. 17-No. 3.
Applicare Medical Imaging B.V., RadWorks Product Line, Version 2.1 Product Catalog, 1997.
Noro R. et al., "Real-Time Telediagnosis of Radiological Images through an Asynchronous Transfer Mode Network: The ARTeMeD Project," Journal of Digital Imaging, Aug. 1997, pp. 116-121, vol. 10-No. 3.
Wakerly R.T. et al., "Planning for the Four Stages of Health Information Network Development," 1996 Annual HIMSS Conference and Exhibition.
Verma R.C. et al., "Picture Archiving and Communication System—Asynchronous Transfer Mode Network in a Midsized Hospital," Journal of Digital Imaging, Aug. 1997, pp. 99-102, vol. 10-No. 3.
Ratib, et al., Self contained off-line media for exchanging medical images using DICOM-complaint standard, Medical Imaging 2000: PACS Design and Evaluation: Engineering and Clinical Issues, Proceedings of SPIE, 2000, pp. 30-34, vol. 3980.
Radiographic Digital Imaging Inc., Cobrascan Presentation, 1999.
Radiographic Digital Imaging Inc., Xscan32 Imaging Software: Version 2.10; Program Guide, 1999.
DR Systems, Inc., Reading Station with Ambassador Product Webpage, Jan. 26, 1998.
Redacted Email regarding "Vepro: Description of Systems," Mar. 26, 1999.
Redacted First Amendment to Apr. 8, 1998 Purchase Agreement between General Electric Co. and VEPRO, dated May 28, 1999.
Redacted Offer from VEPRO to GE Medical Systems for MEDIMAGE Digital Film Recording & CD-R Archiving Station/19" Monitor Color, Upgrades, and Installation, dated Mar. 4, 1999.
Redacted Purchase Agreement between General Electric Co. and VEPRO, dated Apr. 8, 1998.
Redacted Purchase Agreement between General Electric Co. and VEPRO, dated Nov. 22, 1999.
Reiber J.H.C. et al., "The effect of DICOM on QCA and clinical trials", Int J Card Imaging, 1998, pp. 7-12, vol. 14-suppl.1.
UCLA Department of Radiological Sciences, UCLA Medical Imaging Division: PACS/Teleradiology: Research and development progress report, Feb. 1995.
Delmater R., "Multi-Media Messaging: An Emerging Vision for Health Care Delivery ," 1996 Annual HIMSS Conference and Exhibition.
Crabtree R.A., "Pay for Extra Performance," 1996 Annual HIMSS Conference and Exhibition.
Graham R.B.H. et al., "Achieving Results: Implementation of Best Practices in Patient Financial Services," 1996 Annual HIMSS Conference and Exhibition.
Skinner R.I. et al., "Ambulatory Information Systems for Managed Care," 1996 Annual HIMSS Conference and Exhibition.
Linderman R.J., "Reengineering Transcription Services to Reduce Costs and Improve Service Quality," 1996 Annual HIMSS Conference and Exhibition.
Wertz R.K., "CD-ROM: A New Advance in Medical Information Retrieval," JAMA, Dec. 26, 1986, pp. 3376-3378, vol. 256-No. 24.
Brandon R.L. et al., "Redesign of Decedent Care System Provides Compassion, Responsiveness, and Security," 1996 Annual HIMSS Conference and Exhibition.
Corley R.P. et al., "Infrastructure Requirements for Rapidly Changing Hospital Delivery Systems," 1996 Annual HIMSS Conference and Exhibition.

Taira R.K. et al., "A Concept-Based Retrieval System for Thoracic Radiology," Journal of Digital Imaging, Feb. 1996, pp. 25-36, vol. 9-No. 1.

Bowman R. et al., "Building and Maintaining Today's Networks," 1996 Annual HIMSS Conference and Exhibition.

Copple R., PE, et al., "Developing a Methodology to Drive Patient Care Unit Consolidation," 1996 Annual HIMSS Conference and Exhibition.

Johnson R.L., "Trends in The Health Care Vendor Marketplace," 1996 Annual HIMSS Conference and Exhibition.

Nelson R. et al., "Outcomes of Telemedicine Services . . . Patient and Medicolegal Issues," 1996 Annual HIMSS Conference and Exhibition.

RSNA '99 Destination Digital, produced in *Datcard* v. *Codonics* Civil Action No. SACV 08-00063 AHS.

Crespin R.J. et al., "Establishing World Wide Web Presence: Guidelines for Health Care Organizations," 1996 Annual HIMSS Conference and Exhibition.

Saha S., "The New Age Electronic Patient Record System," Proceedings of the 1995 Fourteenth Southern Biomedical Engineering Conference, Apr. 7-9, 1995, pp. 134-137.

Sales Order Packing Slip, Trex Medical Corp., dated Jun. 27, 2000.

Williams S. et al., "The Inside Story on Chin Implementation: CIO's First Hand Experience," 1996 Annual HIMSS Conference and Exhibition.

Lafrance S., "Security vs. Access: A New Health Care Dilemma," 1996 Annual HIMSS Conference and Exhibition.

Perry J.H., Selections from: A generic hospital PACS RFP presented to the Seventh RIS-PACS School Georgetown University Medical Center, Jul. 9, 1997.

Software Engineering Corp., SENCOR Part Ten (X)—SPX100, Jan. 3, 2001.

GE Medical Systems, Senographe 2000 D Review WorkStation DICOM V3.0 Conformance Statement, 2003.

Dorenfest S.I., CPA, MBA, "Emerging Trends in Health Care Information Systems: Increasing Focus on Process Improvement Benefits Through Clinical Automation," 1996 Annual HIMSS Conference and Exhibition.

Miller S., "Selecting and Implementing Local Facilities and Services from Competitive Providers," 1996 Annual HIMSS Conference and Exhibition.

Shipping Checklists and FedEx Manifests from Mitra Imaging to Electromed International, dated Sep. 5, 1997 and Sep. 12, 1997.

Hipax-Steinhart Medizinsysteme, Short Instructions: DICOM Communication, 1999.

Siemens, DICOM 3.0 Conformance Statement, DICOMLink v1.2 for ICON, 1998.

Siemens Health Services, Sienet—DICOM Conformance Statement: MagicView 50 Versions VA10A, VA10B and VA10C Revision 2.0, Nov. 13, 1997.

Siemens Medical Systems, Inc., ACOM.CONVERT DICOM Conformance Statement, Sep. 15, 1999.

Siemens Medical Systems, Inc., ACOM.M/B 2.2 Basic System DICOM Conformance Statement, May 21, 1999.

Siemens Medical Systems, Inc., ACOM.Report VA01A DICOM Conformance Statement (Sep. 17, 1999).

Siemens Medical Systems, Inc., ACOM.Report VA02A DICOM Conformance Statement (Dec. 21, 2001).

Siemens Medical Systems, Inc., ACOM.Web VA21A DICOM Conformance Statement (Mar. 9, 2000).

Siemens Medical Systems, Inc., ACOM.Web VA21C DICOM Conformance Statement (Mar. 21, 2001).

Siemens Medical Systems, Inc., Fast, secure, reliable Sienet Enterprise PACS (1998).

Siemens Medical Systems, Inc., MagicView 1000 Softcopy reading with advanced 3D processing customized to your preferences (1998).

Siemens Medical Systems, Inc., MagicView 300 Enterprise-wide clinician viewing of images and reports (1998).

Siemens Medical Systems, Inc., MagicView CT/MR (1999).

Siemens Medical Systems, Inc., PACS Planning & Integration Services (1998).

Siemens Picture Archiving and Communication System Proposal for Huntsville Hospital, dated Apr. 8, 1999.

Siemens SIENET DICOM Conformance Statement MagicView 300 Version VA30A, Revision 8.0, Copyright 2000.

Siemens Sienet MagicView 50 Teleradiology System Webpage, Ovid Technologies, Inc., Copyright 2000-2007.

Siemens, SIENET MagicView 300, Copyright Apr. 2001.

Sienet MagicStore VB22D DICOM Conformance Statement, Siemens Health Services, dated May 11, 2000.

SIENET Sky DICOM Conformance Statements Webpage, Siemens Healthcare, Copyright 2002-2008.

Sohard AG, Radin Version 2.0, dated Nov. 2002, Screen Captures.

Solicitation for Digital Imaging Network—Picture Archiving and Communication System, Jan. 21, 1997.

Sonya Donaldson, Kodak Picture CD—Software Review—Evaluation (Oct. 2000).

Sorna, FilmX Sell Sheet, dated Mar. 3, 2000.

Seshadri S.B., "Market Scan: PACS Market Migrates to 'Early Majority' Users," Diagnostic Imaging, pp. 207-211, dated Nov. 1997.

Wiebe S., "Information Systems Planning For An Urban/Rural Integrated Delivery System," 1996 Annual HIMSS Conference and Exhibition.

Pomerantz S.M., M.D., "First Person: Soft-Copy Interpretation Finally Surpasses Film," Diagnostic Imaging, pp. 37-39, dated Mar. 1998.

Smith S.M., Cpt., "Mailed Appointment Reminders: An Analysis of Their Cost-Effectiveness," 1996 Annual HIMSS Conference and Exhibition.

Neal S. et al., "Case Study: Interactive Video Communications in Health Care," 1996 Annual HIMSS Conference and Exhibition.

Horii S.C., M.D., "Informatics: Workstation Priorities: Automation, Integration," Diagnostic Imaging, pp. 40-45, dated Jan. 1998.

Dowding S.K', "On the Road to Staff Reengineering," 1996 Annual HIMSS Conference and Exhibition.

TDK Electronics Corp., Invoice (2000-2001).

TDK Medical, Medical CD Recording Station Planning and Installation Manual (2001).

TDK Medical, Quotation and Technical Specification: TDK's CDRS-1100AD (Jul. 17, 2003).

TDK Medical, Quotation and Technical Specification: TDK's CDRS-1100AUTOTP (Jul. 17, 2003).

Barbaras L. et al., The All-Digital Department Moves to the Web, Clinical Data on the WWW, 1996.

Erickson B.J. et al., The Evolution of Electronic Imaging in the Medical Environment, Journal of Digital Imaging, Aug. 1998, pp. 71-74, vol. 11-No. 3-Supp 1.

The Imaging Resource, The Imaging Resource Digital Photography Newsletter, vol. 1, No. 3 (Oct. 22, 1999).

Tape T.G. et al., "Designing A Clinician User-Interface For A Health Care InformationSystem,"1996 Annual HIMSS Conference and Exhibition.

Hendershott T.H., "Evaluating Process Change Proposals In An Outpatient Pharmacy Using Simulation," 1996 Annual HIMSS Conference and Exhibition.

Smith T.W. et al., "Are You Really Ready for CHINs?," 1996 Annual HIMSS Conference and Exhibition..

Wilson T.B., "Healthcare Handoffs Across a Wide Area: A Groupware Solution," 1996 Annual HIMSS Conference and Exhibition.

Rickards T., "What is DISC Birmingham 96?" Jul. 24, 1996.

Rickards T., DICOM Tutorial: ESC Annual Meeting Birmingham, Aug. 1996.

Holden T.D. et al., "Nuts and Bolts Approach to Project Management," 1996 Annual HIMSS Conference and Exhibition.

TREXnet HR DICOM Media Conformance Statement, Trex Medical Corp., dated Jun. 29, 1998.

TREXnet HR Price Book, dated 2000.

U.S. Department of Health and Human Services, Food and Drug Administration, Center for Devices and Radiological Health, Guidance for Industry—Guidance for the Submission of Premarket Notifications for Medical Image Management Devices (Jul. 27, 2000).

UCSF Radiological Informatics Research: A Progress Report, Feb. 1996.

UCSF Radiological Informatics Research: A Progress Report, Feb. 1997.

Universal Connectivity: Now and tomorrow, Radiological Society of North America, Founded in 1915.
User Manual for MEDIMAGE: DICOM Archiving & Viewing Station, Vepro Computersysteme, dated May 9, 2000.
User's Guide for ImageAXS Pro-Med (Windows), Digital Arts & Sciences, Copyright 1998.
User's Manual for Medical Imaging and Communication System (Version 3), HiPax, Copyright 2000.
Kenney A.R. et al., Using a Kodak Photo Cd Technology for Preservation and Access: A Guide for Librarians, Archivists, and Curators, "Web links confirmed as of Apr. 30, 1998.".
Kuzmak P.M. et al., Using Experience with Bidirectional HL7 — ACR-NEMA Interfaces between the Federal Government HIS/RIS and Commercial PACS to Plan for DICOM, SPIE, 1995, pp. 132-143, vol. 2435.
UTech Product Brochure, UTech Products, Inc., dated Nov. 28, 1997.
Van Meurs B.F.A., "Information management in the cardiology department. An analysis of current options for replacing cinefilm", Int J Card Imaging, 1995, pp. 159-163, vol. 11-suppl.3.
Vepro Computersysteme GmbH, "Cardio-Viewing Station," dated 1997.
Vepro Computersysteme GmbH, "Readme," dated Sep. 16, 1997.
Vepro Computersysteme Gmbh, "MEDIMAGE®: The Image Management System: DICOM Archiving & Viewing Station: Software Vers. 4.42," Pfungstadt, Germany, dated Jan. 26, 2000.
Vepro Computersysteme Gmbh, 510(K) Summary (Jun. 6, 1997).
Vepro Computersysteme Gmbh, MEDIMAGE The Image Management System—ACOM.Convert DICOM Archiving & Viewing Station , Software Vers. 4.42 (May 9, 1999).
Vepro Computersysteme Gmbh, MEDIMAGE The Image Management System—Digital Film Recording Station, Software Version 4.40 (Oct. 28, 1999).
Vepro Computersysteme GmbH, Medimage: DICOM Archiving & Viewing Station, Software Vers. 4.42, User-Manual, dated May 9, 2000.
Vepro Computersysteme, Email re: MEDIMAGE Cardio/Angio Viewing Station; MEDIMAGE Image Server; MEDIMAGE CD-ROM Jukebox Server; MEDIMAGE DICOM 3.0 Server Akquisition Station; CARDIO—Viewing Station; MEDIMAGE Digital Filmrecording & CD-R Archiving Station (Dec. 22, 1997).
Vepro Gmbh, Invoices re: MEDIMAGE Cardio/DICOM Viewing Software (1998).
Vepro MedImage Disc, Paediatrische Kardiologie Univ. Heidelberg: INF 150-153, 69120 Heidelberg, dated Apr. 28, 1999.
Vepro Medimage Printout, Pädiatrische Kardiologie Universitatsklinik Heidelberg: INF 150-153, 69120, dated Jan. 30, 2009.
Vepro, 17 Years Computer Experience; Company Profile; Letter re: Software Evaluation; Email re: Software Evaluation (Feb.-Mar. 1998).
Vepro, Cardio-Network, dated Feb. 19, 1999.
Vepro, Centura Health Purchase Order Confirmation, dated Sep. 30, 1999.
Vepro, Centura-Porter Advertist Hospital Training Reports, dated 1999.
Vepro, Certificate for the Quality Assurance System (Feb. 12, 2004).
Vepro, Diagram of a Digital Cath-Lab, dated Feb. 19, 1999.
Vepro, Medlmage Cardio Viewing Station Extended, Version 4.41. 03, "About Cardio Viewing Station," dated 1998.
Vepro, Medlmage Cardio Viewing Station Extended, Version 4.41. 05, "About Cardio Viewing Station," dated 1999.
Vepro, Product Sheet: Image/Film Archive, Server, dated Feb. 19, 1999.
Vepro, Product Sheet: Image/Film Jukebox Server, dated Feb. 19, 1999.
Vepro, Purchase Order from Centura Health, dated Sep. 30, 1999.
Vepro, Serial Number Records for Project Denver, dated Nov. 25, 1999.
Vepro, Viewing Software Handbook, Viewing Software Version 4.41 (Oct. 7, 1998).
Weston V. et al., "Reengineering And Technology—Building A Strong Foundation For The CPR," 1996 Annual HIMSS Conference and Exhibition.
Voxar, Plug 'n View 3d 2.1 (Demonstration), "readme.txt," dated Nov. 12, 1999.
Peterson B.W., "Strategies for Ambulatory Care Scheduling," 1996 Annual HIMSS Conference and Exhibition.
Gray W.M., FHIMSS et al., "Planning and Developing Of A Statewide Health Information Network," 1996 Annual HIMSS Conference and Exhibition.
Dejarnette W., Web Technology and its Relevance to PACS and Teleradiology, Applied Radiology, Aug. 2000, pp. 9-12.
Weterings R.A.M., "Integrated image storage solution for the Cath department", Int J Card Imaging, 1998, pp. 349-356, vol. 14.
Andrew W.F. et al., "The Computer-Based Patient Record: An Essential Technology for Healthcare," 1996 Annual HIMSS Conference and Exhibition.
Crawford W.H. et al., "EIS Unplugged," 1996 Annual HIMSS Conference and Exhibition.
Ahrens W.J. et al., "The Help Desk and the Integrated Clinical Information System, " 1996 Annual HIMSS Conference and Exhibition.
Vrooman W.P. et al., "Benefits Realization Analysis Of A Clinical Information System," 1996 Annual HIMSS Conference and Exhibition.
Work Orders from Mitra Imaging to Electromed International, dated May 1, 1998.
Arenson R.L. et al., Clinical evaluation of a medical image management system for chest x-rays. AJR, 1988; pp. 55-59, vol. 150.
Arenson R.L. et al., The overlapping domains and interface between radiology information management system and medical image management system (PACS), Proceedings of Computer Assisted Radiology, 1987, pp. 855-865, Springer-Verlag, Berlin, Germany.
Cao F. et al., Medical image security in a HIPAA mandated PACS environment. Computer Med. Imaging and Graphics, 2003, pp. 185-96, vol. 27.
First Consulting Group for the American Hospital Association: The Impact of the Proposed HIPAA Privacy Rule on the Hospital Industry. Dec. 2000.
Fischer H.W.: Radiology Departments: Planning, Operation, and Management. Ann Arbor, MI; Edwards Brothers, Inc. 1982: Chapter 7; Communication: 263-273.
Federal Register, 45 C.F.R. Part 142, Security and Electronic Signature Standards; Proposed Rule, Part III. Aug. 12, 1998.
Health Insurance Portability and Accountability Act, 1996, various statements and materials pertaining to the legislation and regulations promulgated thereunder ("HIPAA").
Heartlab DicomView User's Guide, Copyright 1998.
Horii S.C., DICOM, Chapter 4 in: Kagadis, G.C., Langer, S.C.: Informatics in Medical Imaging. CRC Press, Boca Raton, FL, 2011: 41-67.
Inamura K., et al.: A trial of PACS employing magneto-optical disks. SPIE vol. 1234 Medical Imaging IV: PACS System Design and Evaluation 1990: 50-59.
Levin K. et al., Methods to prefetch comparison images in image management and communication systems (IMAC). Proceedings of SPIE 1980; 1234: 270-274.
Ligier Y. et al., Distributed file management for remote clinical image viewing stations. Proceedings of SPIE 1996; 2711: 475-482.
Mascarini CH. et al., In-house access to PACS images and related data through World Wide Web. Proceedings of SPIE 1996; 2711: 531-537.
Nissen S.E., "Evolution of the Filmless Cardiac Angiography Suite: Promise and Perils of the Evolving Digital Era," Copyright 1996.
"DISC'95," Copyright 1995.
Seshadri S.B. et al., An image archive with the ACR/NEMA message formats. Proceedings of SPIE 1988; vol. 914:1409-1415.
Seshadri S.B. et al.: The architecture of an optical jukebox image archive. SPIE vol. 1234 Medical Imaging IV; PACS System Design and Evaluation 1990; 925-932.
Heartlab Website Excerpts of www.Heartlab.com , from The Internet Wayback Machine.(Archive.Org), Copyright 1999.
http://medical.nema.org/dicom/workshop-03/pres/mildenberger.ppt The DICOM Story (presented at the DICOM Anniversary and Workshop, Baltimore, MD, Sep. 2003). Last accessed: Oct. 31, 2011.
Microsoft Visual Basic-Programming for Windows v. 4.0, 1995.
Hunt W.J., The C Toolbox, 1985.

Okura Y. et al: Archiving and Networking of Medical Motion Picture Employing DVD-RAM and MPEG-2. CARS' 99, p. 1064, Jun. 23-26, 1999.

ESC DISC'96 Tutorial, Aug. 1996.

eFilm and eFilmLite Screen Grabs, Feb. 2000.

eFilm Release Notes, dated Feb. 18, 2000.

Section 9.1.5 from Digital Imaging and Communications in Medicine (DICOM) Part 8: Network Communication Support for Message Exchange, dated 2003, 2004, 2006-2008.

Time Stamp Counter—Wikipedia, the free encyclopedia, http://en.wikipedia.org/wiki/Time_Stamp_Counter, last visited Apr. 27, 2012.

Gips, M.A. "PCs at Peace," Security Management, Dec. 1, 1997.

Elion, J.L.: DICOM Media Interchange Standards for Cardiology: Initial Interoperability Demonstration. 19th Annual Symposium on Computer Applications in Medical Care, 1995, pp. 591-595.

U.S. Appl. No. 13/368,286, filed Feb. 7, 2012, Wright et al.

U.S. Appl. No. 13/368,288, filed Feb. 7, 2012, Wright et al.

U.S. Appl. No. 13/168,302, filed Feb. 7, 2012, Wright et al.

SYSTEM FOR REMOTELY GENERATING AND DISTRIBUTING DICOM-COMPLIANT MEDIA VOLUMES

CROSS-REFERENCE TO RELATED APPLICATIONS

This application is a continuation of U.S. application Ser. No. 11/740,062, filed on Apr. 25, 2007, and entitled "SYSTEM FOR REMOTELY GENERATING AND DISTRIBUTING DICOM-COMPLIANT MEDIA VOLUMES", which claims priority to U.S. Provisional Patent Application Ser. No. 60/795,141, filed on Apr. 26, 2006, and entitled "SYSTEM FOR REMOTELY GENERATING AND DISTRIBUTING DICOM-COMPLIANT MEDIA VOLUMES", the content of each of which is incorporated herein in its entirety.

FIELD OF THE INVENTION

The present invention relates to systems for generating and distributing media volumes containing digital image data, and more particularly to systems for remotely generating and distributing digital image data-recorded media volumes through electronically-transmitted commands.

BACKGROUND OF THE INVENTION

Modern healthcare facilities now regularly utilize digital imaging modalities such as magnetic resonance (MR), computer tomography (CT), digital radiography, and ultrasound devices. These modalities, referred to as input imaging devices, produce vast numbers of diagnostic quality digital medical images. In order to more easily manage and distribute such digital images, many healthcare facilities rely upon compact recordable media, such as optically-recordable compact discs (CD) and digital video discs (DVD).

A formatting standard that is commonly used in the healthcare industry for recording such digital image data is the Diagnostic Imaging and Communications in Medicine (DICOM) standard. Through such a format, electronic data supporting digital images are recorded onto recordable media volumes as DICOM objects. The generation and recordation of such DICOM objects requires specific dedicated equipment, hardware, and software. While many facilities operate their own DICOM-compliant volume generation systems, some facilities find that owning, maintaining, and operating their own systems is expensive, and other facilities do not have the demand to justify owning, maintaining, and operating their own equipment. As such, there is a need in the art for systems that are capable of remotely receiving data and instruction from a healthcare facility to generate and distribute DICOM-compliant data object media volumes.

It is therefore a principal object of the present invention to provide a network-based system for receiving digital image data and instructions, and for generating DICOM-compliant media volumes comprising such digital image data, and automatically distributing such recorded media volumes to desired recipients.

It is a further object of the present invention to provide a network-based system for remotely generating and distributing DICOM-compliant media volumes containing user-specified sets of digital image data.

It is a further object of the present invention to provide an automated system which enables remote generation of digital image data-containing media volumes in a DICOM-compliant format, and for automatically labeling and shipping such media volumes to one or more desired recipients, while further automatically invoicing the requesting user.

SUMMARY OF THE INVENTION

By means of the present invention, media volumes containing digital image data, such as that captured from medical imaging modalities, may be generated at a site remote from the facility employing the imaging equipment. The recorded media volumes, which are typically used for medical information records, diagnoses, and the like, may be generated through the instruction and direction of personnel located remote from the media volume recording equipment. Specifically, the system and method of the present invention enables computer network access and control of remote digital image recording equipment.

In a particular embodiment, the system for generating digital image media volumes includes a digital image terminal for receiving, processing, and transmitting digital image data, with the digital image terminal being adapted for processing the digital image data into one or more discrete DICOM-standard data objects. The system preferably further includes a media volume production facility remotely located from the digital image terminal, and communicatively coupled to the digital image terminal via a server-operated computer network. The media volume production facility includes a data recorder device for operably recording the DICOM-standard data objects to the digital image media volumes.

In some embodiments, the DICOM-standard data objects further include cataloging data relevant to the respective digital image data. Such cataloging data may include patient study information, patient series information, patient personal information, digital image attributes, and combinations thereof.

The media volume production facility may further include a shipping label printer for printing shipping labels containing shipment recipient information that is parsed from the cataloging data and is transmitted to the shipping label printer from the server.

The media volume production facility may also include a packaging station for automatically affixing the shipping labels to packaging containing one or more respective digital image media volumes.

The system may also include an invoicing module for automatically generating and transmitting invoices to a digital media volume ordering entity upon receipt of a digital media volume order at the server.

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figure which is intended to be representative of various embodiments of the invention. Other embodiments and aspects of the invention are recognized as being within the grasp of those having ordinary skill in the art.

Figure 1:
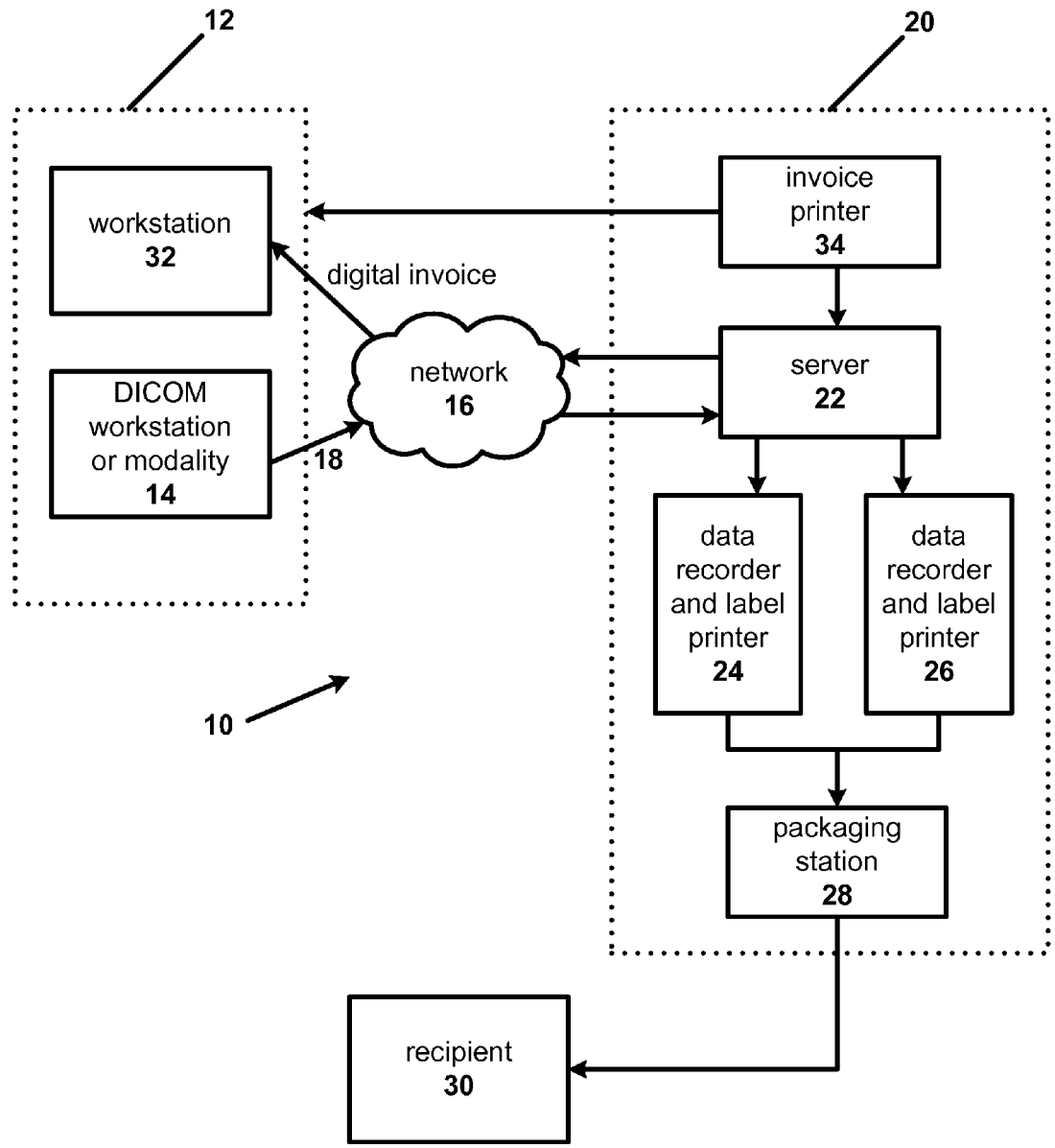
FIG. 1 is a schematic diagram of the system of the present invention.

With reference now to FIG. 1, system 10 of the present invention involves a healthcare facility schematically illustrated at 12, which healthcare facility 12 includes one or more DICOM terminals 14 that receive and collate digital image data from a variety of digital image modalities utilized at healthcare facility 12. In preferred embodiments, DICOM terminal 14 is configured for processing the digital image data in a DICOM-compliant format, so as to generate DICOM-standard objects representing the digital images received from various sources within healthcare facility 12.

In preferred embodiments of the present invention, the one or more DICOM terminals 14 are operably coupled to a network 16 through a network connection 18. Network 16 may be one or more of a variety of network types, such as local area networks (LAN) such as intranets, wide area networks (WAN) such as a global communication network (Internet), and the like. Connection to such network 16 may be accomplished through a variety of network connection types, and through various communication protocols. Examples include Ethernet, DSL, Cable, radio frequency, and other wired or wireless connections. In some embodiments, the use of an application, plug-in and/or a web browser may be required in allowing DICOM terminal 14 to communicate and submit data objects outside of a DICOM network. Accordingly, such application, plug-in, or web browser may be an additional feature required at DICOM terminal 14 for communication to network 16, as illustrated in FIG. 1. Preferably, network connection 18 is suitable for transmitting raw digital image data and/or DICOM-standard objects representing such digital images and relevant cataloging information.

Preferably, network 16 is further communicatively coupled to remote media volume production facility 20, and particularly to a server 22 that is located at, or in communication with facility 20. Although facility 20 is illustrated in FIG. 1 as being contained in a single location, it is contemplated by the present invention that such facility 20 may be distributed among a variety of distinct locations. Specifically, facility 20 need only represent a theoretical grouping of one or more of the components illustrated as being contained with facility 20.

Server 22 preferably receives electronic image data from DICOM terminal 14 through network 16. As described above, such electronic image data may be in the form of DICOM-formatted data objects. In addition to the image data itself, the DICOM objects may further include cataloging data relevant to the image data. This cataloging data includes, for example, patient information, study and series information, date of image, healthcare facility, recipient information, and the like. The DICOM objects preferably include a hierarchy beginning with the patient having one or more studies, with each study including one or more series. Each series identified in each study includes one or more discrete image data files. For example, a particular patient may have one study conducted by digital radiography (DR), and another study by ultrasound (US). If that patient has had two separate visits to the healthcare facility wherein images of both types described above were obtained, each visit will comprise a series of the respective study. Moreover, each series may involve a plurality of images defined by a plurality of image data files which are obtained at the visit for each imaging modality.

DICOM terminal 14 may preferably utilize a plug-in module that is specifically configured to create and submit orders to server 22 in conformity with predetermined guidelines. Such a module permits any digital image creating source to utilize the service of the present invention without having to separately provide appropriate software.

The digital image data and the cataloging data may then be utilized by server 22 to direct data recorder device 24 to record DICOM-compliant data objects onto one or more media volumes, with such media volumes typically comprising optically-recordable compact discs, digital video discs, blue-ray discs, and the like. A variety of devices may be utilized data recorded device 24, such as compact disc recorders, digital video disc recorders, and the like. Such recording equipment is commonly referred to as "burners" and utilize laser energy to scribe an optically-readable pattern in the relevant media (CDs, DVDs, etc.). A particular system that may be useful in recording DICOM-compliant data objects onto one or more media volumes is described in U.S. Pat. No. 7,120,644, herein incorporated by references. Moreover, server 22 is preferably programmed to transmit at least certain of the cataloging data received from DICOM terminal 14 to a shipping label printer 26 for generation of one or more shipping labels that reflect the desired recipient of the recorded media volumes generated by data recorder 24. Such recipients are preferably identified at healthcare facility 12 and transmitted to facility 20 via network 16 in the cataloging data associated with the respective DICOM object(s).

In preferred embodiments, the one or more recorded media volumes contain digital image data recorded in a DICOM part 10 format for DICOM 3.0 objects. In some embodiments, each of such recorded media volumes further include a DICOM directory, and optionally one or more DICOM viewers. Preferably, each recorded media volume is labeled on its surface in data recorder device 24 through conventional mechanisms.

The one or more recorded media volumes pertinent to a particular order from healthcare facility 12 is then packaged at packaging station 28, including the affixation to the packaging of the shipping label generated at shipping label printer 26. Such packaged media volumes are then shipped to the appropriate recipient 30.

As a further feature of system 10 of the present invention, server 22 is preferably programmed to transmit invoices for the relevant orders received from healthcare facility 12 through one or both of electronic transmission and/or hardcopy transmission. As shown in FIG. 1, electronic transmission is preferably accomplished through network 16 in a similar fashion as the data receipt described above. Such electronic invoices are preferably received by a work station 32 at healthcare facility 12. In some embodiments, server 22 transmits electronic data to an invoice printer 34, which generates a hardcopy invoice, with such hardcopy invoices being subsequently shipped to healthcare facility 12.

Figure 2:
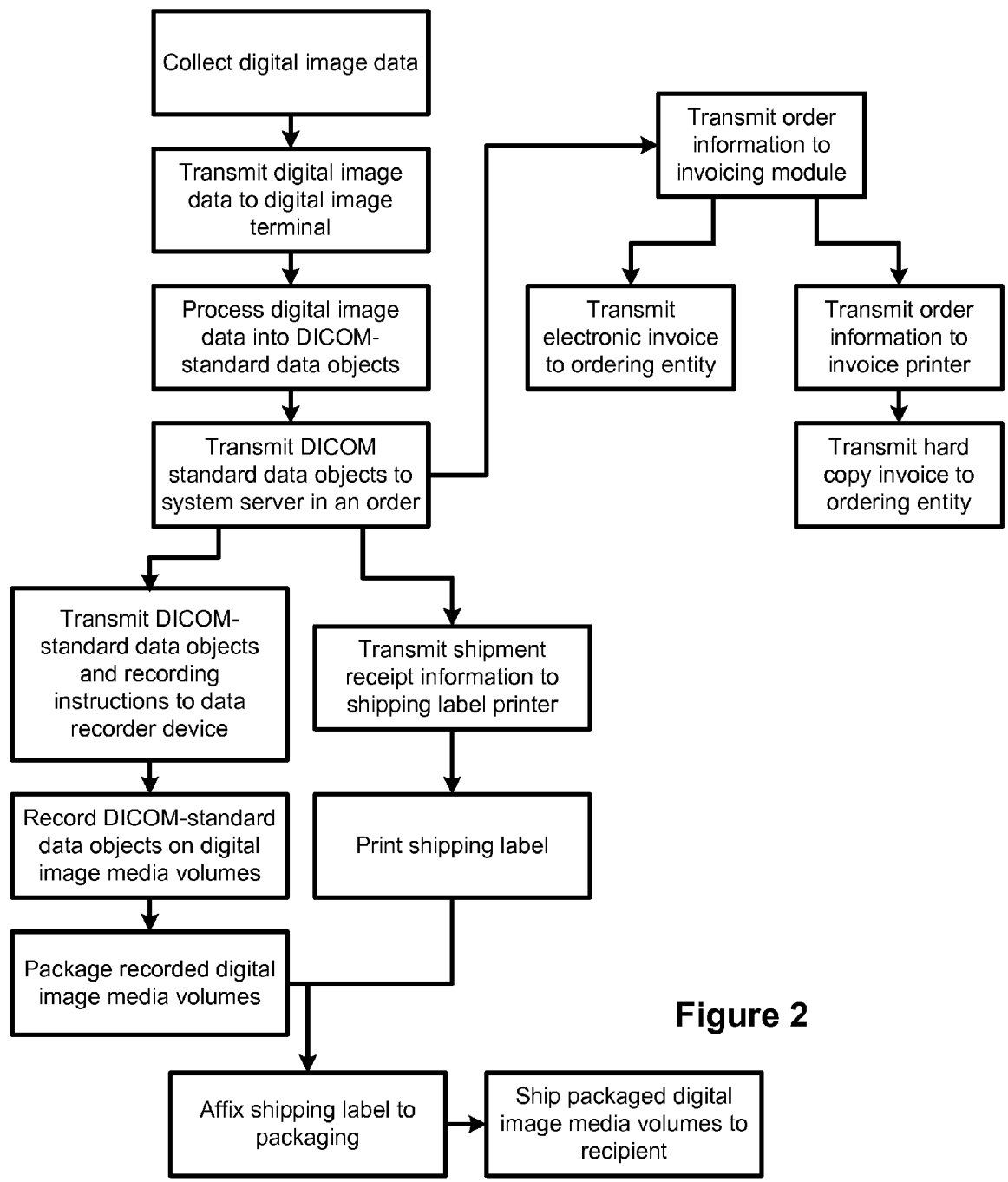
FIG. 2 is a flow diagram demonstrating a method of the present invention.

As demonstrated in the flow diagram of FIG. 2, a method of the present invention involves collecting digital image data on one or more of a variety of digital image capturing modalities, and transmitting such digital image data to a digital image terminal. The raw digital image data is preferably converted or processed into DICOM-standard data objects that each embody one or more discrete digital images. In some embodiments, digital image terminal 14 may include software that is specifically programmed to process raw digital image data into DICOM-standard data objects. An example of such software is eFilm, available from MERGE Healthcare of Milwaukee, Wis. Accordingly, digital image terminal 14 may include digital processing means and software necessary to perform the processing of raw digital image data collected from the various medical imaging modalities into DICOM-standard data objects.

In some embodiments, the DICOM-standard data objects created at digital image terminal 14 are transmitted to a system server 22 in the form of a digital image media volume order. Such an order may include raw digital image data instead of, or in addition to, DICOM-standard data objects containing such raw digital image data. The order transmitted to system server 22 preferably includes attributes for defining instructions in recording the DICOM-standard data objects on one or more digital image media volumes. Such attributes are therefore transmitted in connection with the DICOM-standard data objects to the data recorder device for generation thereat of one or more digital image media volumes containing such DICOM-standard data objects.

The attributes associated with the DICOM-standard data objects preferably further include shipment recipient information correlating to the digital image media volumes to be generated. Such shipment recipient information is accordingly transmitted to a shipping label printer for generation of shipping labels thereat. The printed shipping labels may be automatically affixed to the recorded digital image media volume packaging at packaging station 28, and placed in shipment to the intended recipient.

The order attributes transmitted to system server 22 are also preferably forwarded to an invoicing module at system server 22 for generation of appropriate invoices. In some cases, the invoicing module of system server 22 generates an electronic invoice based upon the order attributes, and transmits such electronic invoice to the ordering entity via network 16. In other embodiments, the invoicing module may instead or additionally transmit the order information to an invoice printer 34, where the hardcopy invoice is generated and prepared for delivery to the ordering entity.

The system described above provides a digital image recording system that remotely generates recorded media volumes for shipment to desired recipients, such as referring physicians or patients. The system of the present invention enables healthcare facilities to obtain and generate such recorded media volumes without the necessity of owning, maintaining, and operating the componentry, as contained in facility 20. As such, significant cost savings are realized by the healthcare facilities.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different methods/devices and that various modifications can be accomplished without departing from the scope of the invention itself.

What is claimed is:

1. A system for generating digital media volumes for distribution to a recipient, the system comprising:
    an interface configured to receive an order to produce a digital media volume containing a user-specified DICOM-standard digital image or set of images for distribution to a recipient;
    a storage module configured to receive medical data captured by one or more modalities;
    a processor communicatively coupled to the interface and the storage module via a computer connection or network, the processor being configured to process the order and access from the storage module the specified DICOM-standard digital image(s), based on the order;
    a data recorder device communicatively coupled to the processor via a computer connection or network, the data recorder device being configured to receive the specified DICOM-standard digital image(s) from the processor and record the specified DICOM-standard digital image(s) to a portable digital media volume that is removable from the data recorder device for distribution to the recipient; and
    a first printer configured to receive textual data associated with the specified DICOM-standard digital image(s) and print a label for the digital media volume based on information regarding the recipient parsed from the data,
    wherein the processor comprises an accounting module configured to generate accounting data using attributes of the order and transmit the accounting data to a computer terminal, based on the creation of the portable digital media volume by the data recorder device.

2. The system of claim 1, wherein the digital media volume is an optically-recordable compact disc (CD) or digital video disc (DVD).

3. The system of claim 1, wherein the textual data comprises patient study information, patient series information, patient personal information, and/or digital image attributes.

4. The system of claim 1, wherein the computer terminal comprises a second printer configured to print a hardcopy containing the accounting data.

5. The system of claim 1, wherein the data recorder device is remotely located from the processor.

6. The system of claim 1, wherein the computer terminal is remotely located from the processor.

7. A computer-implemented method for generating digital media volumes comprising:
    receiving an order to produce a digital media volume containing a user-specified DICOM-standard file or set of files for distribution to a recipient;
    accessing from at least one storage module the specified DICOM-standard file(s) and textual data associated with the DICOM-standard file(s), based on the order;
    with a data recorder device, generating a digital media volume that is removable from the data recorder device, the digital media volume containing the specified DICOM- standard files(s);
    with a first printer, receiving the associated textual data and printing a label for the digital media volume based on information regarding the recipient parsed from the textual data; and
    generating accounting data using attributes of the order and transmitting the accounting data to a computer terminal, based on the creation of the portable digital media volume by the data recorder device.

8. The method of claim 7, wherein the digital media volume is an optically-recordable compact disc (CD) or digital video disc (DVD).

9. The method of claim 7, wherein the textual data comprises patient study information, patient series information, patient personal information, and/or digital image attributes.

10. The method of claim 7, wherein the computer terminal comprises a second printer configured to print a hardcopy containing the accounting data.

11. The method of claim 7, wherein the data recorder device is remotely located from the processor.

12. The method of claim 7, wherein the computer terminal is remotely located from the processor.

* * * * *